United States Patent [19]

Hoppe et al.

[11] Patent Number: 5,223,633
[45] Date of Patent: Jun. 29, 1993

[54] PREPARATION OF SEC. OR TERT. ALCOHOLS

[75] Inventors: Dieter Hoppe, Kiel; Petra Tebben, Brunsbuettel; Folker Hintze, Hanover; Thomas Raffel, Bremen, all of Fed. Rep. of Germany

[73] Assignee: Bayer Aktiengesellschaft, Leverkusen, Fed. Rep. of Germany

[21] Appl. No.: 837,713

[22] Filed: Feb. 19, 1992

Related U.S. Application Data

[63] Continuation-in-part of Ser. No. 718,711, Jun. 21, 1991.

[30] Foreign Application Priority Data

Jun. 30, 1990 [DE] Fed. Rep. of Germany ....... 4020942

[51] Int. Cl.$^5$ .......................... C07F 7/22; C07F 7/08; C07C 269/00
[52] U.S. Cl. ..................................... 556/95; 556/478; 560/25; 568/831
[58] Field of Search .................. 556/478, 95; 568/831; 560/25

[56] References Cited

PUBLICATIONS

Reggelin et al., Tetrahedron Letters, vol. 30, No. 22, pp. 2915–2918 (1989).
R. Thornton Morrison et al., Organic Chemistry, (1983), 4th ed., p. 205.
J. March, Advanced Organich Chemistry, p. 222, Table 1 (1985).
T. A. Hase, "Umpoled Synthons", p. 101 (1987).
Morrison and Boyd, "Structure and Properties", pp. 22–25 (1983).

*Primary Examiner*—Paul J. Killos
*Assistant Examiner*—Porfirio Nazario
*Attorney, Agent, or Firm*—Sprung Horn Kramer & Woods

[57] ABSTRACT

A process for the preparation of a compound of the formula

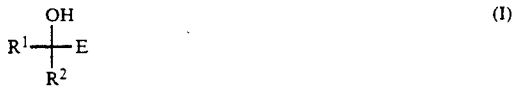

which comprises deprotonating a carbamate of the formula

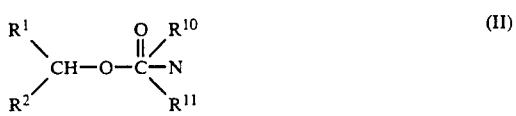

in an inert solvent with a selective base, in the presence of a chelate-forming diamine to give a compound of the formula

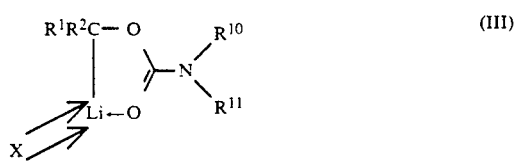

and then reacting III in an inert solvent, either with an achiral electrophile of the formula (IV) or (V) or with an optionally prochiral electrophile of the formula (VI)

G—Y, (IV)

CO$_2$, (V)

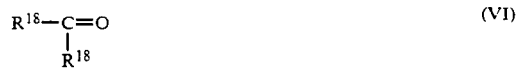

and in the case in which $R^1$ represents an electrofugic leaving group, optionally again electrophilically substituted with the formation of an acyl anion and renewed deprotonation, and in a last step, solvolytically removing the protecting group —CO—NR$^{10}$R$^{11}$.

5 Claims, No Drawings

PREPARATION OF SEC. OR TERT. ALCOHOLS

This is a continuation-in-part of application Ser. No. 718,711, filed Jun. 21, 1991, now pending.

The invention relates to a new process for the preparation of compounds, some of which are known, containing sec.- or tert.-alcohol groups, via α-oxycarbanions, which are important intermediates for the synthesis of pharmaceutically active compounds, in particular for the synthesis of renin-inhibitory and HIV protease-inhibitory peptides.

It is already known that α-oxyalkylcarbanions can be employed as umpoled synthons in the electrophilic introduction of α-hydroxy-alkyl radicals and in the Wittig reaction [cf. J.E. Saavedra in T.A. Hase (ed.) "Umpoled Synthons", p. 101, Wiley 1987].

It is additionally known that the α-oxyalkylcarbanions could hitherto only be prepared directly by cleavage of α-stannyl ethers with transmetallation, by reductive cleavage of monothioacetals with lithium naphthalenide or by deprotonation of some sterically hindered benzoates [cf. J. Am. Chem. Soc. 1977, 99, 5213].

However, these processes have great disadvantages owing to the use of large amounts of bases to increase the deprotonation rate, the poor removability of the protecting groups (arylcarbonyl radical) and the low yield.

The preparation of the corresponding non-racemic chiral α-oxyalkyllithium compounds, which are stable in terms of configuration, is likewise only possible via a stereo-specific cleavage of the enantiomerically pure stannanes, which is usually associated with a complicated diastereomer separation.

The invention relates to a process for the preparation of compounds containing sec.- and tert.-alcohol groups of the general formula (I)

(I)

in which

R¹ represents hydrogen or an electrofugic leaving group, or represents straight-chain or branched alkyl or alkenyl in each case having up to 10 carbon atoms which are optionally substituted by alkoxy having up to 6 carbon atoms, phenyl or by the group —NR³R⁴,
in which
R³ and R⁴ are identical or different and denote hydrogen, straight-chain or branched alkyl having up to 8 carbon atoms, phenyl or benzyl, R² represents hydrogen, or R¹ and R² together form a 3- to 7-membered cycloalkyl ring
and E represents straight-chain or branched alkyl or alkenyl in each case having up to 8 carbon atoms which are optionally monosubstituted to trisubstituted by hydroxyl, phenyl or cycloalkyl having 3 to 7 carbon atoms or are substituted by a group of the formula —NR³R⁴, —HN—CO—OR⁵, —SiR⁶R⁷R⁸ or SnR⁶'R⁷'R⁸',
in which R³ and R⁴ have the abovementioned meanings
and R⁵ denotes straight-chain or branched alkyl having up to 6 carbon atoms, which is optionally substituted by phenyl, R⁶, R⁷, R⁸, R⁶', R⁷' and R⁸' are identical or different and denote straight-chain or branched alkyl having up to 6 carbon atoms, represents cycloalkyl or cycloalkenyl having 3 to 7 carbon atoms, which is optionally substituted by hydroxyl, represents carboxyl, alkoxycarbonyl having up to 4 carbon atoms or a group of the formula —SiR⁶R⁷R⁸, —SnR⁶'R⁷'R⁸' or R⁹—CO,
in which R⁶, R⁶', R⁷, R⁷', R⁸ and R⁸' have the abovementioned meanings
and R⁹ denotes hydrogen or straight-chain or branched alkyl or alkenyl in each case having up to 8 carbon atoms which are optionally monosubstituted to trisubstituted by phenyl or by the group of the formula —NH—CO—OR⁵,
in which R⁵ has the abovementioned meaning, which is characterized in that carbamates of the general formula (II)

in which

R¹ and R² have the abovementioned meaning
and

R¹⁰ and R¹¹ are identical or different and either represent straight-chain or branched alkyl having up to 8 carbon atoms, or together with the nitrogen atom represent a radical of the formula

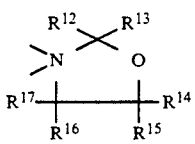

in which

R¹², R¹³, R¹⁴, R¹⁵, R¹⁶ and R¹⁷ are identical or different and represent hydrogen, straight-chain or branched alkyl having up to 8 carbon atoms, aryl having 6 to 10 carbon atoms or cycloalkyl having 3 to 8 carbon atoms, or in each case R¹² and R¹³, R¹⁴ and R¹⁵ and/or R¹⁶ and R¹⁷ together form a 3- to 6-membered carbocycle, are quantitatively deprotonated in inert solvents using selective bases, in the presence of a chelate-forming diamine which, if appropriate, is chiral (designated by X in the following), to give compounds of the general formula (III)

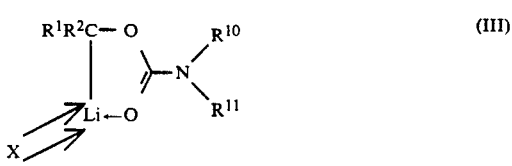
(III)

in which

R$^1$, R$^2$, R$^{10}$ and R$^{11}$ have the abovementioned meanings, which, in the case of a chiral diamine such as (−)-sparteine takes place enantioselectively, and them substituted in inert solvents, either with achiral electrophiles of the general formulae (IV) and (V) or with electrophiles which, if appropriate, are prochiral, of the formula (VI)

$$G-Y, \quad (IV)$$

$$CO_2. \quad (V)$$

$$\underset{R^{18'}}{R^{18}-C=O} \quad (VI)$$

in which

G has the abovementioned meaning of E and is identical to or different from this, but does not represent hydrogen or carboxyl, Y represents halogen, R$^{18}$ and R$^{18'}$ are identical or different and have the abovementioned meaning of R$^9$ or R$^{18}$ and R$^{18'}$ together form a cyclobutyl, cyclopentyl or cyclohexyl ring or either R$^{18}$ or R$^{18'}$ represents a nucleofugic leaving group, and in the case in which R$^1$ represents a typical leaving group, optionally electrophilically substituted again with the formation of an acyl anion and renewed deprotonation, and in a last step, if appropriate in the presence of auxiliaries, the protecting group —CO—NR$^{10}$R$^{11}$ is solvolytically removed.

In the above substituent definitions, R$^{10}$ and R$^{11}$ preferably represent alkyl having up to 4 carbon atoms, in particular isopropyl or, together with the nitrogen atom, a radical of the formula

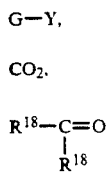

Preferred chiral diamines of the substituent X which may be mentioned are: tetramethylethylenediamine (TMEDA) and (−)-sparteine.

Halogen preferably represents fluorine, chlorine or bromine, in particular chlorine. and in a last step, solvolytically removing the protecting group —CO—NR$^{10}$R$^{11}$.

In the above substituent definitions, R$^{10}$ and R$^{11}$ preferably represent alkyl having up to 4 carbon atoms, in particular isopropyl or, together with the nitrogen atom, a radical of the formula

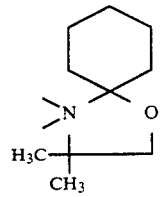

Preferred chiral diamines of the substituent X which may be mentioned are: tetramethylethylenediamine (TMEDA) and (−)-sparteine.

Halogen preferably represents fluorine, chlorine or bromine, in particular chlorine.

The first process according to the invention can be illustrated by way of example by the following equation:

The process according to the invention can be illustrated by way of example by the following equation:

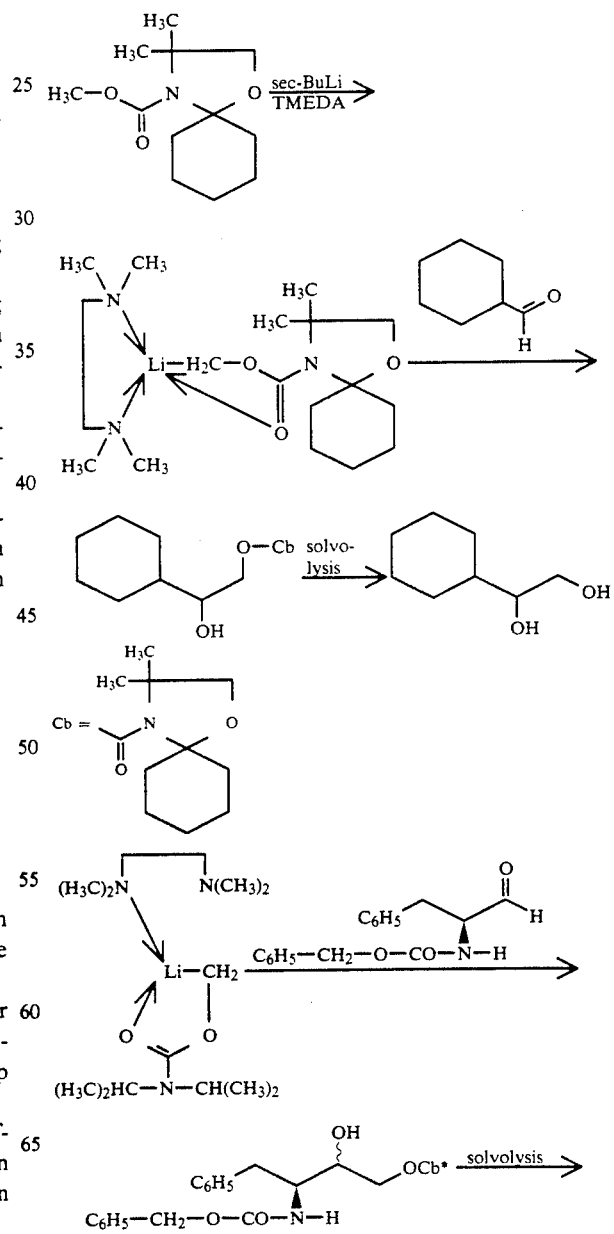

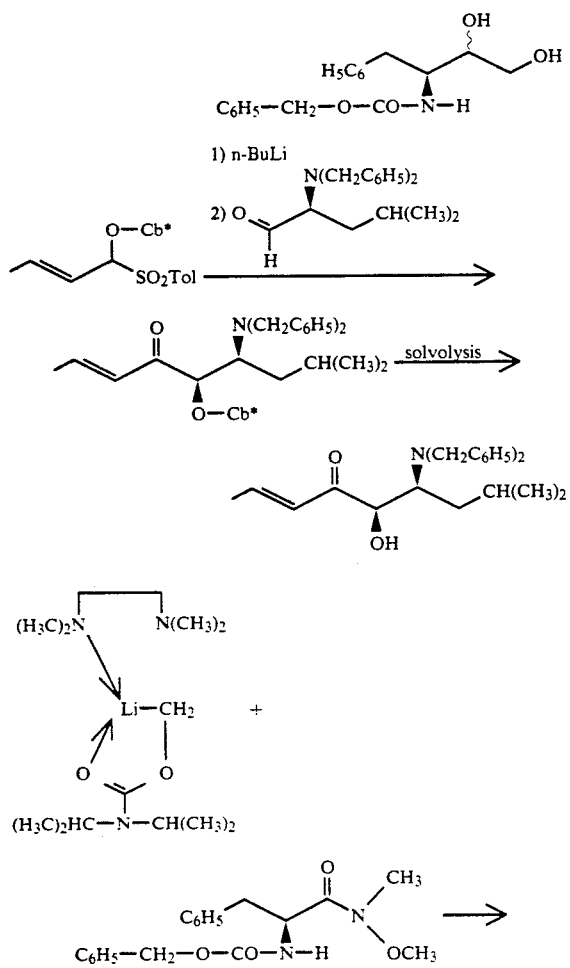

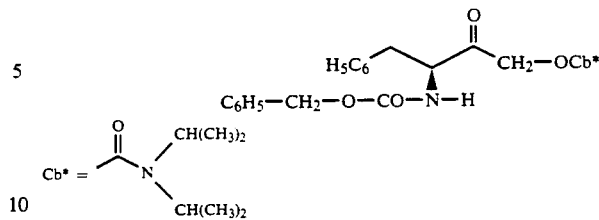

Surprisingly, the process according to the invention yields the desired compounds of the general formula (I) in good yields.

The process is distinguished by several advantages: in contrast to the prior art, the carbamic acid esters, as protecting groups, can be easily introduced and removed. In addition, stoichiometric amounts of bases, preferably sec.-butyllithium, are adequate for deprotonation. In addition, the process according to the invention enables both control of the diastereoselectivity by the choice of achiral or prochiral electrophilic substituents and influence of asymmetric induction with prochiral carbamates in the presence of chiral complex-forming diamines.

By means of the use of enantiomerically pure diamine compounds such as, for example, (−)-sparteine, deprotonation of the compounds of the formula (II) takes place enantioselectively and in very good yields to give the corresponding chiral compounds, preferably to give the (S)-lithium compounds of the formula (III), which can then be converted by further reaction, for example with chlorotrimethylstannane or carbon dioxide, to the corresponding carboxylic acid derivatives, preferably in the R-configuration.

Enantioselective deprotonation is illustrated by way of example by the following equation:

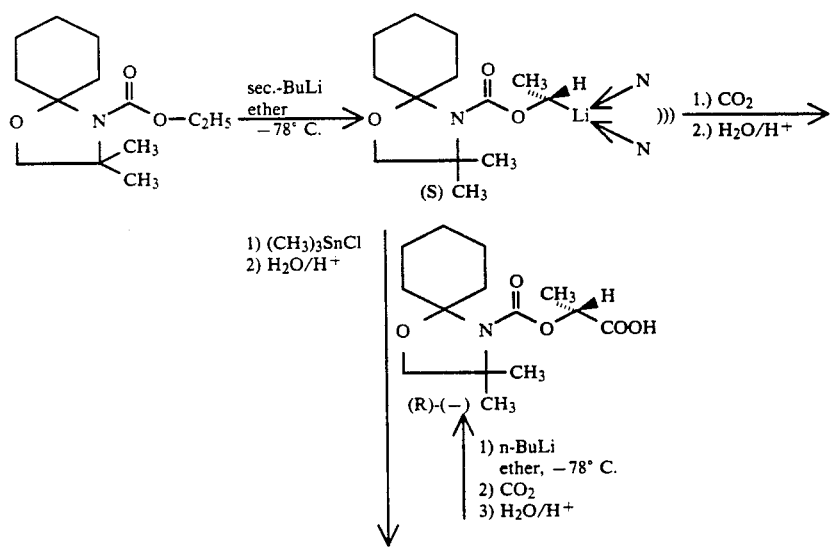

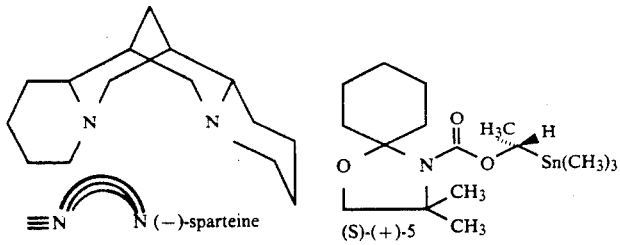

Formula (I) provides a general definition of the compounds prepared by the process according to the invention.

If $R^1$ in the context of the abovementioned definition represents a typical leaving group, then it preferably represents a group which is customary in substitution reactions, from the series comprising: chlorine, bromine, iodine, tosylate, mesylate or the radical $-O-SO_2CF_3$.

Compounds of the general formula (I) preferably prepared by the process, according to the invention are those
in which
$R^1$ represents hydrogen or the group

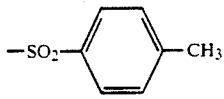

represents straight-chain or branched alkyl or alkenyl in each case having up to 8 carbon atoms which are optionally substituted by alkoxy having up to 4 carbon atoms, phenyl or by the group $-NR^3R^4$,
in which
$R^3$ and $R^4$ are identical or different and denote hydrogen, straight-chain or branched alkyl having up to 6 carbon atoms, or benzyl,
$R^2$ represents hydrogen, or
$R^1$ and $R^2$ together form the cyclopentyl ring
and
E represents straight-chain or branched alkyl or alkenyl in each case having up to 6 carbon atoms which are optionally monosubstituted to trisubstituted by identical or different substituents from the series comprising hydroxyl, phenyl, cyclobutyl, cyclopentyl, cyclohexyl or by a group of the formula $-NR^3R^4$, $-NH-CO-OR^5$, $-SiR^6R^7R^8$ or $-SnR^{6'}R^{7'}R^{8'}$,
in which
$R^3$ and $R^4$ have the abovementioned meanings,
$R^5$ denotes straight-chain or branched alkyl having up to 4 carbon atoms, which is optionally substituted by phenyl,
$R^6$, $R^{6'}$, $R^7$, $R^{7'}$, $R^8$ and $R^{8'}$ are identical or different and denote straight-chain or branched alkyl having up to 4 carbon atoms,
represents cyclobutyl or cyclohexyl which are optionally substituted by hydroxyl,
represents carboxyl, methoxycarbonyl or a group of the formula $-SiR^6R^7R^8$, $-SnR^{6'}R^{7'}R^{8'}$ or $R^9-CO-$,
in which
$R^6$, $R^{6'}$, $R^7$, $R^{7'}$, $R^8$ and $R^{8'}$ have the abovementioned meanings
and
$R^9$ denotes hydrogen or straight-chain or branched alkyl or alkenyl in each case having up to 6 carbon atoms which are optionally monosubstituted to trisubstituted by phenyl or by a group of the formula $-NH-CO-OR^5$,
in which
$R^5$ has the abovementioned meaning.

Compounds of the general formula (I) particularly preferably prepared by the process according to the invention are those
in which
$R^1$ represents hydrogen or alkyl having 1-4 C atoms,
$R^2$ represents hydrogen,
E represents straight-chain or branched alkyl or alkenyl in each case having up to 4 carbon atoms which are optionally monosubstituted to trisubstituted by identical or different substituents from the series comprising hydroxyl, phenyl, cyclobutyl, cyclohexyl or by a group of the formula $-NR^3R^4$, $-NHCO-OR^5$, $-SiR^6R^7R^8$ or $-SnR^{6'}R^{7'}R^{8'}$
in which
$R^3$ and $R^4$ are identical or different and denote hydrogen, straight-chain or branched alkyl having up to 4 carbon atoms or benzyl,
$R^5$ denotes methyl or ethyl which are optionally substituted by phenyl,
$R^6$, $R^{6'}$, $R^7$, $R^{7'}$, $R^8$ and $R^{8'}$ represent methyl,
represents cyclobutyl or cyclohexyl which are optionally substituted by hydroxyl,
represents carboxyl, methoxycarbonyl or a group of the formula $-SiR^6R^7R^8$, $-SnR^{6'}R^{7'}R^{8'}$ or $R^9-CO-$,
in which
$R^6$, $R^{6'}$, $R^7$, $R^{7'}$, $R^8$ and $R^{8'}$ have the abovementioned meanings
and
$R^9$ denotes hydrogen or straight-chain or branched alkyl or alkenyl in each case having up to 4 carbon atoms which are optionally monosubstituted to trisubstituted by phenyl or by a group of the formula $-NH-CO-OR^5$,
in which
$R^5$ has the abovementioned meaning.

Suitable solvents for the deprotonation are preferably inert organic solvents such as hydrocarbons such as hexane, pentane, ligroin or toluene, and ethers, for example tetrahydrofuran, diethyl ether, dioxane, dimethoxyethane, diglyme, triglyme or tert.-butyl methyl ether. Tetrahydrofuran and diethyl ether are particularly preferred.

Deprotonation is carried out in a temperature range from $-100°$ C. to room temperature, preferably at about $-78°$ C. to $0°$ C.

Deprotonation can be carried out both at normal pressure and at elevated or reduced pressure (for example 0.5 to 2 bar), preferably at normal pressure.

Suitable selective bases are alkyllithium compounds having up to 6 C atoms in the alkyl group, preferably n-butyllithium or sec.-butyllithium.

The base is employed in an amount from 0.5 to 5 mols, preferably in stoichiometric amounts.

Electrophilic substitution is also carried out in the abovementioned solvents, preferably in tetrahydrofuran at normal pressure.

Electrophilic substitution is carried out in a temperature range from about $-100°$ C. to $+40°$ C., preferably in the range from $-78°$ C. to room temperature.

The removal of the protecting groups (carbamic acid esters) is carried out by a customary method by means of sequential treatment with acids and bases, preferably in methanol.

Suitable acids are strong inorganic acids and organic sulphonic or carboxylic acids such as, for example, methanesulphonic acid, ethanesulphonic acid, benzenesulphonic acid, toluenesulphonic acid, acetic acid or propionic acid.

Suitable bases are alkali metal and alkaline earth metal hydroxides such as, for example, sodium hydroxide, potassium hydroxide or barium hydroxide. Barium hydroxide is preferred.

The acids and bases are employed in an amount from 0.01 to 10 mols, preferably 1 mol.

The removal of the carbamate protecting groups is carried out at a normal pressure in a temperature range from $0°$ C. to $+130°$ C., preferably from $+20°$ C. to $+100°$ C.

Enantioselective deprotonation proceeds under the conditions (solvent, temperature, pressure) which were mentioned above for deprotonation.

The compounds of the general formula (II) are known per se or can be prepared, for example, by reacting amines of the general formula

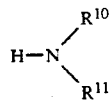

with compounds of the general formula $$Z-CO-O-CHR^1R^2$$

in which $R^1$, $R^2$, $R^{10}$ and $R^{11}$ have the abovementioned meanings
and Z represents chlorine,
in inert solvents.

The preparation of the starting compounds of the formula (II) may be described by way of example in the following:

16.9 g of 3,3-dimethyl-1-oxa-4-azaspiro[4.5]decane are added at room temperature to a solution of 4.73 g (50.0 mmol) of ethyl chloroformate in 50 ml of methylene chloride. After subsequently stirring for 15 hours, the reaction mixture is added to 2 N hydrochloric acid, and the aqueous phase is extracted twice with ether and then neutralized with saturated sodium hydrogen carbonate solution. The compound methyl 3,3-dimethyl-1-oxa-4-azaspiro[4.5]decane-4-carboxylate of the formula

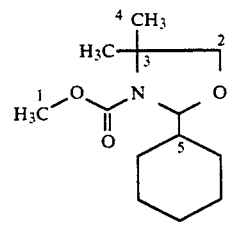

b.p. 125° C./8 torr.
m.p.: 32°–33° C. (from the melt).
$R_f=0.63$ (ether/n-pentane=1:1).
IR (KBr): 1700 cm$^{-1}$ (C=O).
is obtained.

In an analogous manner, the compound ethyl 3,3-dimethyl-1-oxa-4-azaspiro[4.5]decane-4-carboxylate

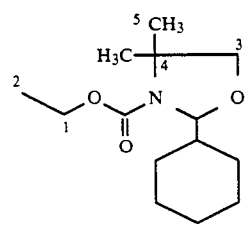

is obtained (yield: 77% of theory).
b.p. 165° C./8 torr.
m.p.: 42° C. (from the melt).
$R_f=0.62$ (ether/n-pentane=1:1).
IR (KBr): 1690 cm$^{-1}$ (C=O).

By reaction of 3,3-dimethyl-1-oxa-4-azaspiro[4.5]decane with trichloromethyl chloroformate, the corresponding carbonyl chloride of the formula

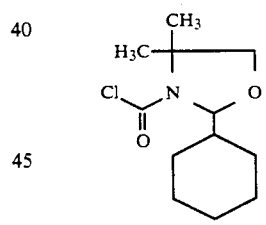

is obtained, which is injected into a suspension of sodium hydride (80% strength paraffin oil) in anhydrous ether and isopropanol and stirred at room temperature for about 4 hours. 1-Methylethyl 3,3-dimethyl-1-oxa-4-azaspiro[4.5]decane-4-carboxylate of the formula

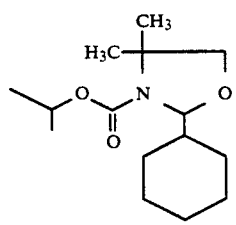

is obtained.
Yield: 90% of theory.
N-(Benzyloxycarbonyl)-(S)-phenylalaninal of the formula

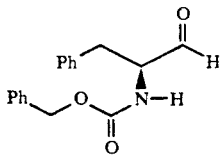

was obtained in an analogous manner.

General Working Procedure I for Metallation of the Carbamates and Reaction of the Anion with Chlorotrimethylsilane 1.0 equivalent of carbamate and 1.1 equivalents of TMEDA are dissolved in anhydrous ether (3 ml/mmol) and treated at −78° C. with 1.1 equivalents of an approximately 1.2N solution of base (for example sec.-BuLi) in cyclohexane/isopentane. To complete lithiation, the reaction mixture is subsequently stirred for 1–5 h, then 1.1 equivalents of chlorotrimethylsilane are injected and the mixture is subsequently stirred at −78° C. for a further hour. For working-up, the reaction mixture is added to 2N hydrochloric acid and ether (10 ml/mmol each), the phases are separated, the aqueous phase is additionally extracted twice with ether, freed from acid with satd. sodium hydrogen carbonate solution and dried over magnesium sulphate, and the solvent is stripped off in vacuo. The crude product is purified by liquid chromatography on silica gel using ether/pentane mixtures.

General Working Procedure II

Metallation with n-BuLi 227 mg (1.0 mmol) of methyl 3,3-dimethyl-1-oxa-4-azaspiro[4.5]decane-4-carboxylate are treated with 1.1 ml of n-BuLi (about 1.6N in n-hexane) and after 5 h with 138 mg (1.1 mmol) of chlorotrimethylsilane. After working up analogously to general working procedure I, 60 mg (20% of theory) of the compound trimethylsilylmethyl 3,3-dimethyl-1-oxa-4-azaspiro[4.5]decane-4-carboxylate of the formula

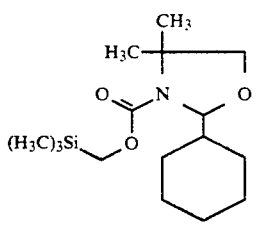

are obtained in addition to 160 mg (70% of theory) of the compound methyl 3,3-dimethyl-1-oxa-4-azaspiro[4.5]decane-4-carboxylate of the formula

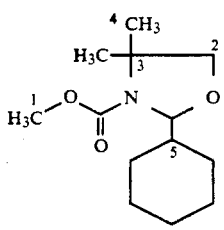

The compound 1-trimethylsilylethyl 3,3-dimethyl-1-oxa-4-azaspiro[4.5]decane-4-carboxylate of the formula

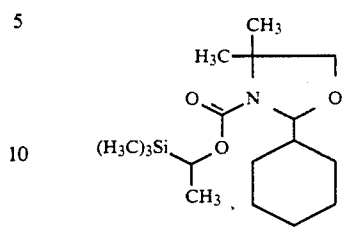

was obtained analogously to this working procedure II.

General Working Procedure III 1.0 equivalent of carbamate and 1.1 equivalents of TMEDA are dissolved in anhydrous ether (3 ml/mmol) and treated at −78° C. with 1.1 equivalents of an approximately 1.2N solution of sec.-BuLi in cyclohexane/isopentane. To complete lithiation, the reaction mixture is subsequently stirred for 1–5 h, then 1.1 equivalents of the electrophile are injected and the mixture is subsequently stirred at −78° C. for 3–15 h. For working-up, the reaction mixture is added to 2N hydrochloric acid and ether (10 ml/mmol, each), the phases are separated, the aqueous phase is additionally extracted twice with ether, freed from acid with saturated sodium hydrogen carbonate solution and dried over magnesium sulphate, and the solvent is stripped off in vacuo. The crude product is purified by liquid chromatography on silica gel using ether/pentane mixtures.

The following compounds were prepared by the process of working procedure III:

2-Hydroxy-3-methylene-4-methylpentyl 3,3-dimethyl-1-oxa-4-azaspiro[4.5]decane-4-carboxylate

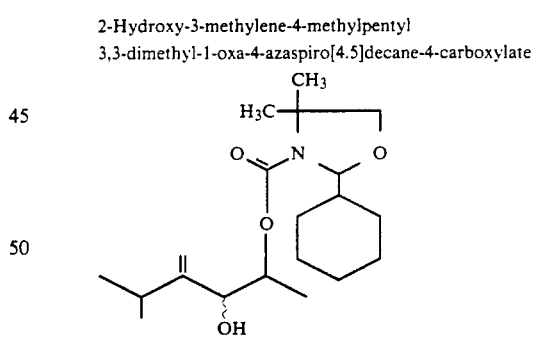

2-Hydroxy-2-cyclohexylethyl 3,3-dimethyl-1-oxa-4-azaspiro[4.5]decane-4-carboxylate

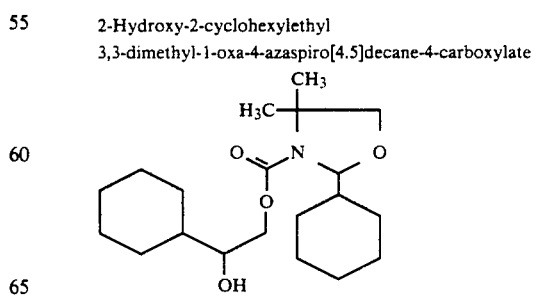

3-Butenyl 3,3-dimethyl-1-oxa-4-azaspiro[4.5]decane-4-carboxylate

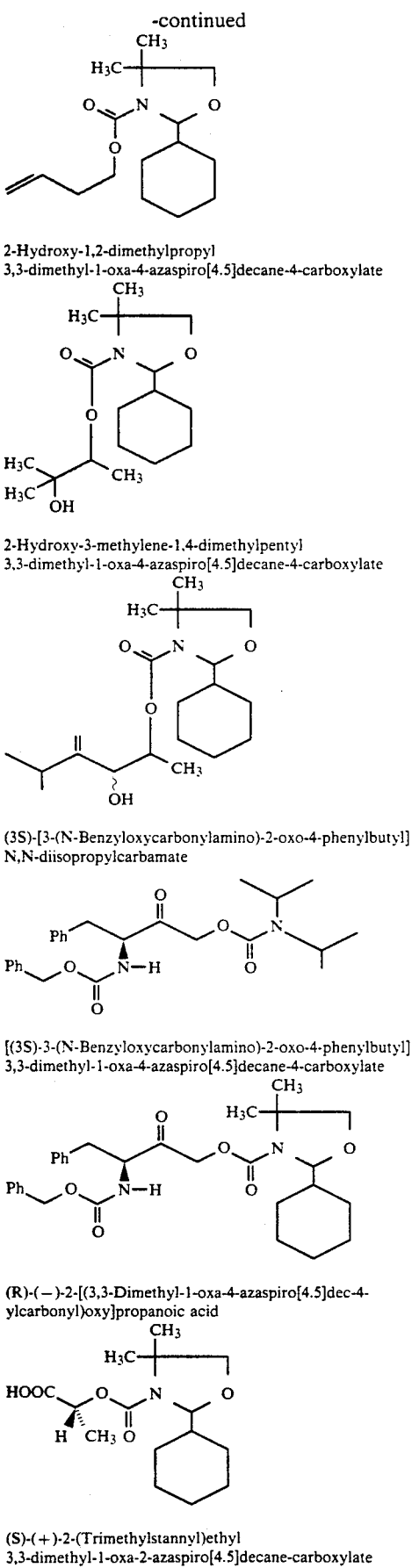

2-Hydroxy-1,2-dimethylpropyl 3,3-dimethyl-1-oxa-4-azaspiro[4.5]decane-4-carboxylate 2-Hydroxy-3-methylene-1,4-dimethylpentyl 3,3-dimethyl-1-oxa-4-azaspiro[4.5]decane-4-carboxylate (3S)-[3-(N-Benzyloxycarbonylamino)-2-oxo-4-phenylbutyl] N,N-diisopropylcarbamate

[(3S)-3-(N-Benzyloxycarbonylamino)-2-oxo-4-phenylbutyl] 3,3-dimethyl-1-oxa-4-azaspiro[4.5]decane-4-carboxylate (R)-(−)-2-[(3,3-Dimethyl-1-oxa-4-azaspiro[4.5]dec-4-ylcarbonyl)oxy]propanoic acid (S)-(+)-2-(Trimethylstannyl)ethyl 3,3-dimethyl-1-oxa-2-azaspiro[4.5]decane-carboxylate

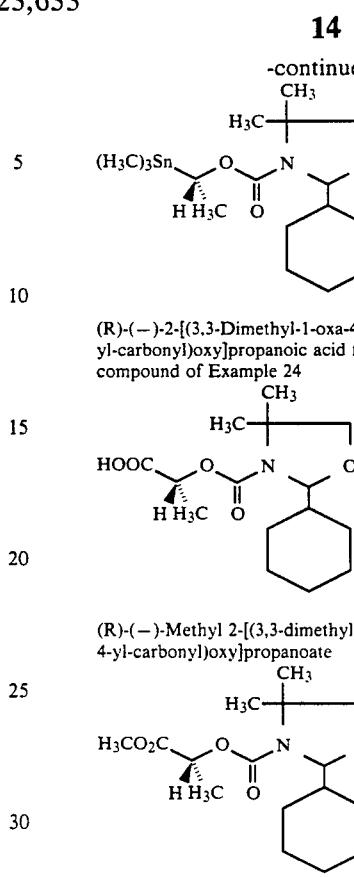

(R)-(−)-2-[(3,3-Dimethyl-1-oxa-4-azaspiro[4.5]dec-4-yl-carbonyl)oxy]propanoic acid from the compound of Example 24

(R)-(−)-Methyl 2-[(3,3-dimethyl-1-oxa-4-azaspiro[4.5]dec-4-yl-carbonyl)oxy]propanoate

General Working Procedure IV 2.9 mmol of (−)-sparteine are added to a solution of 2.8 mmol of sec-BuLi (in cyclohexane/isopentane) in 8 ml of ether cooled to −78° C. After stirring for 10 min, a solution of 2.0 mmol of ethyl 3,3-dimethyl-1-oxa-4-azaspiro[4.5]decane-4-carboxylate in 2 ml of ether is injected and the mixture is stirred at −78° C. for 5–6 hours. After introducing excess carbon dioxide into the solution of the abovementioned compound as the (−)-sparteine complex (for the synthesis of Examples 4–10) or addition of 3.5 mmol of trimethyltin chloride or methyl iodide (for the synthesis of Examples 11–15), the reaction mixture is stirred at −78° C. for 16 hours. For working-up, after warming to room temperature it is poured into 10 ml of ether/10 ml of 2N HCl, extracted twice with 20 ml of ether each time, the combined organic phases are dried over $NaHCO_3/Na_2SO_4$ (1:2) or only over $Na_2SO_4$ (for Examples 4–10) and the crude product is purified by flash chromatography on silica gel using ether/pentane mixtures. The rac-TMEDA racemates are generated in the same manner, but using 2.9 mmol of TMEDA instead of (−)-sparteine.

To remove the Cbx group, 2 mmol of the compounds of Examples 4–15 are treated with 10 ml of methanol and 0.1 ml of methanesulphonic acid and kept under reflux for 16 hours. 1.0 g of $Ba(OH)_2 \cdot 8 H_2O$ are then added and the mixture is heated under reflux for a further 4 hours. For working-up, it is poured into 10 ml of 2N HCl (which is optionally saturated with KCl), extracted three times with 20 ml of ether each time, the ether solution is dried over $Na_2SO_4$ and the crude product is purified on silica gel by flash chromatography.

The examples shown in Tables 1–4 are prepared by working procedure IV.

TABLE 1

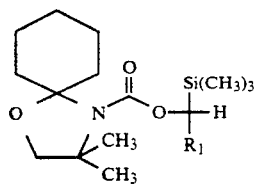

| Ex. No. | $R_1$ | Electrophile | Yield (% of theory) | $[\alpha]_D^{20-23}$ | ee[%] |
|---|---|---|---|---|---|
| (rac)1[a] | H | $(CH_3)_3SiCl$ | 97 | — | — |
| (rac)2[a] | $CH_3$ | $(CH_3)_3SiCl$ | 70 | — | — |
| (S) 3 | $CH_3$ | $(CH_3)_3SiCl$ | 67 | $-22.5^b$ | — |

TABLE 2

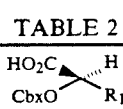

| Ex. No. | $R_1$ | Electrophile | Yield (% of theory) | $[\alpha]_D^{20-23}$ | ee[%] |
|---|---|---|---|---|---|
| (rac)4[a] | $CH_3$ | $CO_2$ | 60 | — | — |
| (R) 5 | $CH_3$ | $CO_2$ | 75 | $-22.3^c$ | >95 |
| (rac)6[a] | $(CH_2)_2CH_3$ | $CO_2$ | 65 | — | — |
| (R) 7 | $(CH_2)_2CH_3$ | $CO_2$ | 78 | $-12.6^c$ | >95 |
| (R) 8 | $(CH_2)_5CH_3$ | $CO_2$ | 62 | — | — |
| (R) 9 | $(CH_2)_5CH_3$ | $CO_2$ | 70 | $-12.4^c$ | >95 |
| (R) 10 | $CH(CH_3)_2$ | $CO_2$ | 52 | $-17.3^c$ | >95 |

TABLE 3

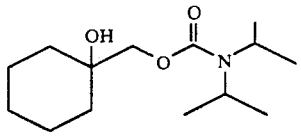

| Ex. No. | $R_1$ | Electrophile | Yield (% of theory) | $[\alpha]_D^{20-23}$ | ee[%] |
|---|---|---|---|---|---|
| (S) 11 | $CH_3$ | $(CH_3)_3SnCl$ | 76 | $+35.4^b$ | >95 |
| (S) 12 | $(CH_2)_2CH_3$ | $(CH_3)_3SnCl$ | 62 | $+35.2^b$ | >95 |
| (S) 13 | $(CH_2)_5CH_3$ | $(CH_3)_3SnCl$ | 86 | $+34.2^b$ | >95 |
| (S) 14 | $CH(CH_3)_2$ | $(CH_3)_3SnCl$ | 62 | $+23.5^b$ | >95 |

TABLE 4

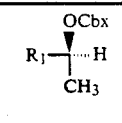

| Ex. No. | $R_1$ | Electrophile | Yield (% of theory) | $[\alpha]_D^{20-23}$ | ee[%] |
|---|---|---|---|---|---|
| (S) 15 | $(CH_2)_5CH_3$ | $CH_3I$ | 81 | $+14.1^c$ | 96 |

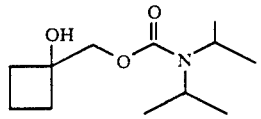

Cl = with TMEDA as a ligand
b = c = 1.4–2.8, $CH_2Cl_2$ $(R_f)$
c = c = 1.1–1.9, acetone $(R_f)$ The following exemplary embodiments represent by way of example the preparation of the compounds of the general formula (I) by the processes according to the invention:

EXEMPLARY EMBODIMENTS

Example 1

(1-Hydroxycyclohexyl)methyl N,N-diisopropylcarbamate 2.2 mmol of sec.-BuLi are added to 318 mg (2 mmol) of methyl N,N-diisopropylcarbamate and 355 mg of TMEDA in 6 ml of THF at an internal temperature of −70° C. to −78° C. After 45 min, the reaction mixture is treated with 98 mg (1 mmol) of cyclohexanone (about 25 mg every 15 min). The reaction is complete after 4 h and the mixture is treated in the cold with 10 ml of 2N hydrochloric acid and 15 ml of ether, warmed to room temperature and the phases are separated. The aqueous phase is extracted twice with ether and the combined organic phases are freed from acid with saturated $NaHCO_3$ solution. After drying over magnesium sulphate, the solvent is stripped off in vacuo and, after chromatographic purification on silica gel using ether/petroleum ether (1:2), 190 mg (74% of theory) of the title compound are obtained as colorless crystals.

$R_f$=0.26 (ether/petroleum ether=1:1, silica gel).

m.p.: 79° C. (n-pentane).

Example 2

(1-Hydroxycyclobutyl)methyl N,N-diisopropylcarbamate 11.148 g (70 mmol) of methyl N,N-diisopropylcarbamate and 12.424 g (105 mmol) of TMEDA in 200 ml of THF are lithiated at −78° C. with 70 mmol of sec. BuLi. After 1 h, 2.453 g (35 mmol) of cyclobutanone are added in portions (about 500 mg every 30 min). The reaction is complete after 3 h (TLC checking) and the reaction mixture is treated in the cold with 100 ml of ether and 120 ml of 2N hydrochloric acid. After warming to room temperature, the phases are separated and the aqueous phase is extracted three times using 50 ml of ether each time. The combined organic phases are then freed from acid with 50 ml of saturated $NaHCO_3$ solution and dried over magnesium sulphate. After the solvent has been stripped off in vacuo, a crude yield of 12.197 g is obtained, chromatographic purification of which on silica gel using ether/petroleum ether (1:1) gives 3.721 g (46.4% of theory) of the title compound as a colorless liquid.

$R_f$=0.24 (ether/petroleum ether=1:1, silica gel).

IR (film): 3430 (OH) and 1670 cm$^{-1}$ (OCON).

$C_{12}H_{23}NO_3$ (229.32)

Calc.: C 62.85 H 10.11.
Found: C 62.86 H 10.24.

Example 3 rac-(2-Hydroxy-3-methylbutyl) N,N-diisopropylcarbamate

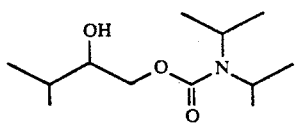

478 mg (3 mmol) of methyl N,N-diisopropylcarbamate are lithiated with 392 mg (3.3 mmol) of TMEDA in 4 ml of THF at −78° C. using 3.3 mmol of sec-BuLi. After 1 h, the reaction mixture is treated with 144 mg (2 mmol) of isobutyraldehyde and stirred for 21 h. The reaction mixture is then treated at −78° C. with 10 ml of 2N hydrochloric acid and 10 ml of ether and the mixture is warmed to room temperature. The phases are separated, the aqueous phase is extracted twice with ether and the combined organic phases are neutralized with saturated NaHCO$_3$ solution. After drying over magnesium sulphate, the solvent is stripped off and the crude product of 500 mg weight is purified by chromatography on silica gel using ether/petroleum ether (1:3). 299 mg (64.6% of theory) of the title compound are obtained as a colorless liquid.

$R_f$=0.26 (ether/petroleum ether=1:1, silica gel).
IR (film): 3400 (OH) and 1670 cm$^{-1}$ (OCON).

$C_{12}H_{25}NO_3$ (231.34)

Calc.: C 62.30 H 10.89.
Found: C 62.39 H 10.89.

Example 4 and Example 5

(2S,3S)-3-(N-Benzyloxycarbonylamino) 2-hydroxy-4-phenyl-butyl-N,N-diisopropylcarbamate (Example 4) and
(2R,3S)-3-(N-benzyloxycarbonylamino) 2-hydroxy-4-phenylbutyl-N,N-diisopropylcarbamate (Example 5)

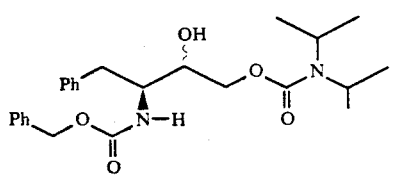

478 mg (3 mmol) of methyl N,N-diisopropylcarbamate and 392 mg (3.3 mmol) of TMEDA in 4 ml of THF are treated at −78° C. with 3 mmol of sec-BuLi. After 30 min, 284 mg (1 mmol) of the compound 3-cyclohexyl-1,2-ethanediol (dissolved in 1.5 ml of THF) are added in the course of 25 min. After 3 h in the cold, the reaction mixture is treated with 7 ml of 2N hydrochloric acid and 10 ml of ether. The phases are separated, the aqueous phase is extracted twice with ether and the combined organic phases are freed from acid with saturated NaHCO$_3$ solution. After drying over magnesium sulphate, the solvent is stripped off in vacuo and 524 mg of a crude product are obtained whose chromatographic purification on silica gel using ethyl acetate/hexane (1:2) gives 116 mg (26% of theory) of the diastereomer Example 18 and 126 mg (29% of theory) of the diastereomer Example 5 as colorless oils.

Example 4

$R_f$=0.55 (ethyl acetate/hexane=1:1, silica gel).
$[\alpha]^{20}_{365}$=−10.1° (c=1.1, dichloromethane).
IR (film): 3420 (OH), 3330 (NH), 1690 (OCON) and 1675 cm$^{-1}$ (OCON).

$C_{25}H_{33}N_2O_5$ (441.55)

Calc.: C 68.01 H 7.53.
Found: C 68.01 H 7.76.

Example 5

$R_f$=0.52 (ethyl acetate/hexane=1:1, silica gel).
$[\alpha]^{20}_D$=−23.1° (c=1.3, dichloromethane).
IR (film): 3420 (OH), 3330 (NH), 1690 (OCON) and 1675 cm$^{-1}$ (OCON).

$C_{25}H_{33}N_2O_5$ (441.55)

Calc.: C 68.01 H 7.53.
Found: C 68.09 H 7.73.

Example 6

Cyclohexyl-1-1,2-ethanediol

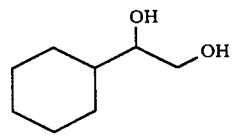

454 mg (2.0 mmol) of the compound from 2-hydroxy-2-cyclohexylethyl 3,3-dimethyl-1-oxa-4-azaspiro[4.5]-decane-4-carboxylate are dissolved in 10 ml of methanol, 1 drop of methanesulphonic acid is added and the reaction mixture is heated under reflux for 15 h. After cooling, the mixture is treated with a large excess of barium hydroxide and heated under reflux for a further 4 h. For working-up, the cooled reaction mixture is poured into 10 ml each of 2N hydrochloric acid and ethyl acetate, the phases are separated, the aqueous phase is extracted twice with ethyl acetate, and the combined organic phases are neutralized with saturated sodium hydrogen carbonate solution and dried over magnesium sulphate. After liquid chromatography on silica gel using ethyl acetate/hexane =1:1, 260 mg (1.8 mmol, 90% of theory) of the title compound are obtained as a colorless solid.

m.p.: 40° C. (ether/pentane).
$R_f$=0.22 (ethyl acetate/n-hexane=1:1).
IR (KBr): 3330 cm$^{-1}$ (OH).

1. New alkylcarbamates

Method A

Example 1 of the formula II:

Heptyl 2,2,4,4-tetramethyl-1,3-oxazolidine-3-carboxylate

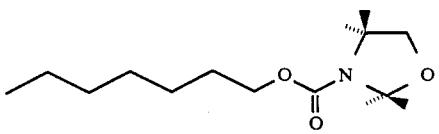

933 mg (8.0 mmol) of n-heptanol were added at room temperature to a suspension of 272 mg (9.2 mmol) of 80 per cent sodium hydride in 10 ml of anhydrous ether. After stirring at room temperature for 30 min, 1.19 g (6.2 mmol) of the carbamoyl chloride CbxCl from Example 1, dissolved in 5 ml of ether, were injected and the mixture was subsequently stirred at room temperature for 72 hours. To work up the reaction mixture, it was poured into 25 ml of 2N HCl. The organic phase was separated off and the aqueous phase was extracted three times with 20 ml of ether each time. The combined organic phases were deacidified and dried over solid sodium hydrogen sulphate and sodium sulphate in the amount ratio 1:2. After the removal of the solvent in vacuo, the crude product was purified by column chromatography on silica gel (ether/n-pentane 1:9). 1.55 g (92%) of the title compound was obtained as a colorless oil. $R_F=0.71$ (silica gel, ether/pentane 1:1).

Example 2 of the formula II:

Heptyl 3,3-dimethyl-1-oxa-4-azaspiro[4.4]nonane-4-carboxylate

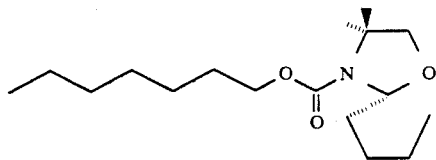

1.70 g (92%) of the title compound were obtained analogously as a colorless oil from 1.35 g (6.2 mmol) of the carbamoyl chloride CbxCl from Example 3, 272 mg (9.2 mmol) of 80 per cent sodium hydride and 933 mg (8.0 mmol) of n-heptanol. $R_F=0.67$ (silica gel, ether/pentane 1:1).

Example 3 of the formula II:

Nonyl 2,2,4,4-tetramethyl-1,3-oxazolidine-3-carboxylate

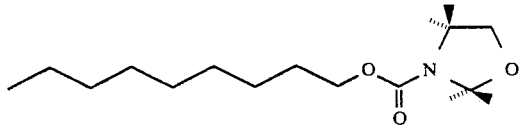

4.70 g (63%) of the title compound were obtained analogously as a slightly yellowish oil from 4.79 g (25 mmol) of the carbamoyl chloride CbyCl from Example 1, 1.10 g (37.2 mmol) of 80 per cent sodium hydride and 4.61 g (31.9 mmol) of n-nonanol. $R_F=0.64$ (silica gel, ether/pentane 1:1).

Example 4 of the formula II:

Hex-5-enyl 2,2,4,4-tetramethyl-1,3-oxazolidine-3-carboxylate

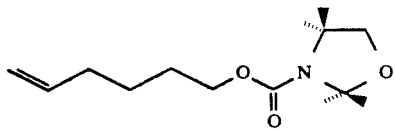

8.83 g (94%) of the title compound were obtained analogously as a colorless oil from 7.04 g (36.7 mmol) of the carbamoyl chloride CbxCl from Example 1, 1.38 g (46.7 mmol) of 80 per cent sodium hydride and 4.04 g (40.3 mmol) of n-hex-5-en-1-ol. $R_F=0.62$ (silica gel, ether/pentane 1:1).

Example 5 of the formula II:

2-(N,N-Dibenzylamino)ethyl 2,2,4,4-tetramethyl-1,3-oxazolidine-3-carboxylate

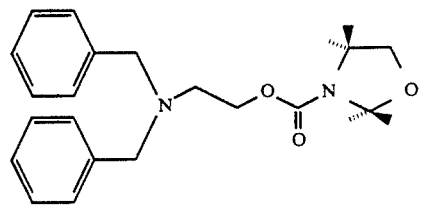

2.41 g (10.0 mmol) of 2-(N,N-dibenzylamino)ethanol, dissolved in 5 ml of dimethoxyethane (DME) were slowly added dropwise to a suspension of 400 mg (14.0 mmol) of sodium hydride (80% in mineral oil) in 20 ml of DME. The mixture was stirred at room temperature for 2 h to completely deprotonate it. 1.91 g (10.0 mmol) of the carbamoyl chloride CbxCl from Example 1, dissolved in 5 ml of DME, were added to this mixture. The reaction mixture was hydrolyzed with 5 ml of water and 15 ml of ether after stirring at room temperature for 5 d. The aqueous phase was additionally extracted three times using 10 ml of ether each time. The combined organic phases were dried over magnesium sulphate and concentrated in vacuo. After separation by column chromatography on silica gel (0.20–0.50; ether/pentane 1:2), 3.61 g (91%) of the title compound were obtained as a colorless oil, which later crystallized in a refrigerator. $R_F=0.51$ (silica gel, ether/pentane 1:1), m.p.: 32° C. (from the melt).

Example 6 of the formula II:

3-(N,N-Dimethylamino)propyl 2,2,4,4-tetramethyl-1,3-oxazolidine-3-carboxylate

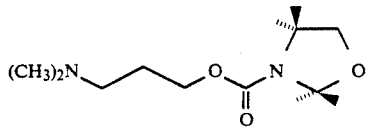

3.77 g (93%) of the title compound were obtained analogously, but using ether as solvent and after purification of the crude product on alumina (ethyl acetate), as a colorless oil from 3.07 g (15.7 mmol) of the carbamoyl chloride CbxCl from Example 1, 847 mg (28.4 mmol) of 80 per cent sodium hydride and 2.11 g (20.5 mmol) of 3-(N,N-dimethylamino)-1-propanol. $R_F=0.44$ (alumina, ethyl acetate).

Example 7 of the formula II:

3-(N,N-Dibenzylamino)propyl 2,2,4,4-tetramethyl-1,3-oxazolidine-3-carboxylate

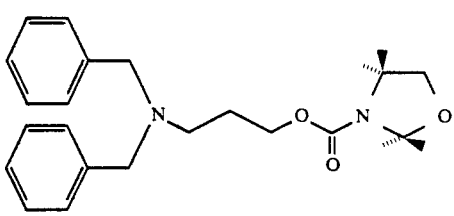

3.53 g (58%) of the title compound were obtained analogously as colorless crystals from 2.87 g (15.0 mmol) of the carbamoyl chloride CbxCl from Example 1, 807 mg (27.0 mmol) of 80 per cent sodium hydride and 4.97 g (19.5 mmol) of 3-(N,N-dibenzylamino)-1-propanol after purification of the crude product on silica gel (ether/pentane 1:1). $R_F=0.41$ (silica gel, ether/pentane 1:2), m.p.: 65° C. (from the melt).

Example 8 of the formula II:

3-(N-Benzyl-N-methylamino)propyl 2,2,4,4-tetramethyl-1,3-oxazolidine-3-carboxylate

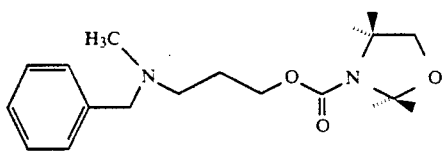

2.71 g (81%) of the title compound were obtained analogously as a colorless oil from 1.96 g (10.0 mmol) of the carbamoyl chloride CbxCl from Example 1, 538 mg (18.0 mmol) of 80 per cent sodium hydride and 2.33 g (13.0 mmol) of 3-(N-benzyl-N-methylamino)-1-propanol after purification of the crude product on silica gel (ether/pentane 1:1). $R_F=0.20$ (silica gel, ether).

Example 9 of the formula II:

4-Methoxybutyl 3,3-dimethyl-1-oxa-4-azaspiro[4.5]decane-4-carboxylate

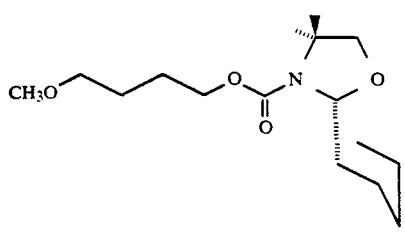

The title compound was obtained analogously, but using THF as solvent, in 83 per cent yield (over both steps) as an orange-yellow oil from 15.50 g (67.0 mmol) of the carbamoyl chloride CbxCl from Example 2, 2.62 g (87.3 mmol) of 80 per cent sodium hydride and 26.78 g (297.5 mmol) of 1,4-butanediol after purification of the crude product on silica gel (ether/pentane 5:1) and the methylation of the product with 1.3 equivalents of sodium hydride and 1.5 equivalents of methyl iodide in ether at room temperature and subsequent purification of the crude product on silica gel (ether/pentane 1:1). $R_F=0.40$ (silica gel, ether/pentane 1:1).

Method B

Example 10 of the formula II:

Ethyl 2,2,4,4-tetramethyl-1,3-oxazolidine-3-carboxylate

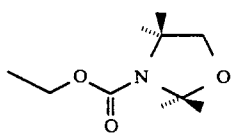

12.11 g (100.0 mmol) of 2,2,4,4-tetramethyl-1,3-oxazolidine (can also be employed in the form of the mixed fraction) were added gradually at room temperature to a solution of 5.43 g (50.0 mmol) of ethyl chloroformate in 50 ml of dry dichloromethane. After stirring for 16 hours, the reaction mixture was poured into 40 ml of 2N HCl. The phases were separated, the aqueous phase was extracted three times with 20 ml of ether each time and the combined organic phases were deacidified and dried over solid sodium hydrogen sulphate and sodium sulphate in the amount ratio 1:2. After the removal of the solvent in vacuo at a maximum of 100 mbar/40° C. bath temperature, the crude product was distilled under reduced pressure. 8.05 g (80%) of the title compound were obtained as a colorless liquid of b.p.: 87° C./10 mbar and $R_F=0.61$ (silica gel, ether/pentane 1:1).

Example 11 of the formula II:

Butyl 2,2,4,4-tetramethyl-1,3-oxazolidine-3-carboxylate

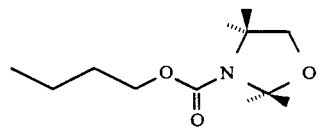

10.89 g (95%) of the title compound were obtained analogously as a colorless oil from 12.92 g (100.0 mmol) of 2,2,4,4-tetramethyl-1,3-oxazolidine and 6.84 g (50.0 mmol) of butyl chloroformate. R, =0.65 (silica gel, ether/pentane 1:1), b.p.: 116° C./17 torr.

2. Lithiation and Reaction With Electrophiles

Example 1 of the formula I':

(S)-(+)-(1-Methylheptyl) 2,2,4,4-tetramethyl-1,3-oxazolidine-3-carboxylate

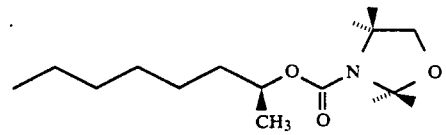

2.8 mmol of a 1.4M sec-butyllithium solution in cyclohexane/isopentane were added to a solution, cooled to −78° C., of 680 mg (2.8 mmol) of (−)-sparteine in 8 ml of anhydrous ether. After stirring at −78° C. for 10 min, a solution of 543 mg (2.0 mmol) of the carbamate from Example 1 of the formula II in 2 ml of ether was added dropwise and the reaction mixture was stirred at −78° C. for 4 hours. After addition of 426 mg (3.0 mmol) of methyl iodide in 2 ml of ether, the reaction was subsequently stirred for 16 hours to complete the reaction, the mixture slowly warming to room temperature. To work up the reaction mixture, it was warmed to room temperature and poured into 10 ml of ether and 10 ml of 2N HCl. The organic phase was separated off, the aqueous phase was extracted three times with 20 ml of ether each time and the combined organic phases were deacidified and dried over solid sodium hydrogen sulphate and sodium sulphate in the amount ratio 1:2. After filtration and removal of the solvent in vacuo, the crude product was purified by chromatography on silica gel (ether/n-pentane 1:10). 491 mg (87%) of the title compound were obtained as a colorless oil of 95% ee. $R_F=0.74$ (silica gel, ether/pentane 1:1), $[\alpha]_D^{19}=+15.40$ (c=1.20, acetone).

Example 2 of the formula I':

(S)-(+)-(1-Methylheptyl) 3,3-dimethyl-1-oxa-4-azaspiro-[4.4]nonane-4-carboxylate

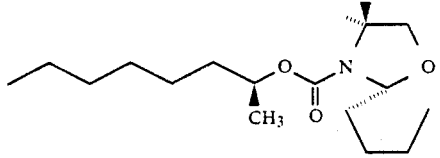

570 mg (92%) of the title compound of 95% ee were obtained analogously from 595 mg (2.0 mmol) of the carbamate from Example 2 of the formula II, 680 mg (2.8 mmol) of (−)-sparteine, 2.8 mmol of sec-butyllithium and 426 mg (3.0 mmol) of methyl iodide after working up and purification on silica gel (ether/pentane 1:9). $R_F=0.80$ (silica gel, ether/pentane 1:1), $[\alpha]_D^{16}=+15.0$ (c=1.65, acetone).

Example 3 of the formula I':

(S)-(+)-(1-Methylbutyl) 2,2,4,4-tetramethyl-1,3-oxazolidine-3-carboxylate

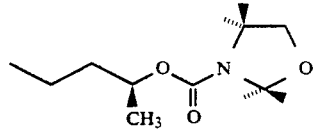

248 mg (51%) of the title compound were obtained analogously as a colorless oil from 459 mg (2.0 mmol) of the carbamate from Example 11 of the formula II, 680 mg (2.8 mmol) of (−)-sparteine, 2.8 mmol of sec-butyllithium and 426 mg (3.0 mmol) of methyl iodide after working up and purification on silica gel (ether/pentane 1:9). $R_F=0.79$ (silica gel, ether/pentane 1:1), $[\alpha]_D^{20}=+17.4$ (c=1.75, acetone).

Example 4 of the formula I':

(R)-(−)-(1-Methyl-but-3-enyl) 2,2,4,4-tetramethyl-1,3-oxazolidine-3-carboxylate

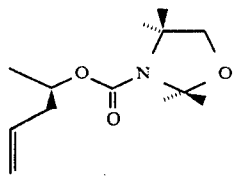

583 mg (60%) of the title compound were obtained analogously as a colorless oil of 42% ee from 804 mg (4.0 mmol) of the carbamate from Example 10 of the formula II, 1.36 g (5.8 mmol) of (−)-sparteine, 5.8 mmol of sec-butyllithium and 762 mg (6.3 mmol) of allyl bromide after working up and purification on silica gel (ether/pentane 1:6). $R_F=0.69$ (silica gel, ether/pentane 1:1), $[\alpha]_{365}^{19}=-3.9$ (c=1.15, acetone).

Example 5 of the formula I':

(R)-(−)-(1,4-Dimethyl-pent-3-enyl) 2,2,4,4-tetramethyl-1,3-oxazolidine-3-carboxylate

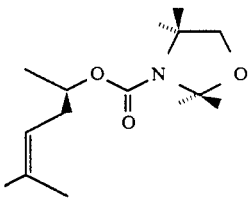

240 mg (45%) of the title compound were obtained analogously as a colorless oil from 403 mg (2.0 mmol) of the carbamate from Example 10 of the formula II, 680 mg (2.8 mmol) of (−)-sparteine, 2.8 mmol of sec-butyllithium and 450 mg (3.0 mmol) of phenyl bromide after working up and purification on silica gel (ether/pentane 1:6). $R_F=0.67$ (silica gel, ether/pentane 1:1), $[\alpha]_{365}^{23}=-4.9$ (c=1.57, CH$_2$Cl$_2$).

Example 6 of the formula I':

(R)-trans-(1-Methyl-hept-3-enyl) 2,2,4,4-tetramethyl-1,3-oxazolidine-3-carboxylate

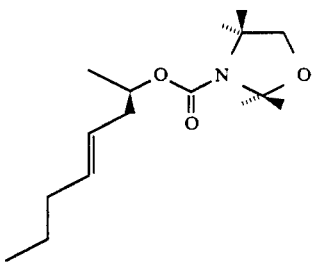

353 mg (62%) of the title compound were obtained analogously as a colorless oil of 22% ee from 403 mg (2.0 mmol) of the carbamate from Example 10 of the formula II, 680 mg (2.8 mmol) of (−)-sparteine, 2.8 mmol of sec-butyllithium and 489 mg (3.0 mmol) of trans-1-bromohex-2-ene after working up and purification on silica gel (ether/pentane 1:6). $R_F=0.67$ (silica gel, ether/pentane 1:1).

Example 7 of the formula I':

(R)-(−)-(1-Methyl-2-phenylethyl)
2,2,4,4-tetramethyl-1,3-oxazolidine-3-carboxylate

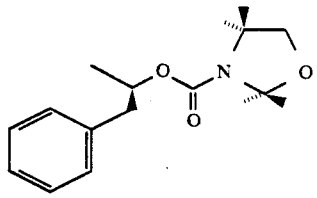

226 mg (39%) of the title compound were obtained analogously as a colorless oil of 44% ee from 403 mg (2.0 mmol) of the carbamate from Example 10 of the formula II, 680 mg (2.8 mmol) of (−)-sparteine, 2.8 mmol of sec-butyllithium and 478 mg (2.8 mmol) of benzyl bromide after working up and purification on silica gel (ether/pentane 1:7). $R_F=0.65$ (silica gel, ether/pentane 1:1), $[\alpha]_{365}^{21} = -35.8$ (c=1.50, acetone).

Example 8 of the formula I':

rac-(1-Methyl-2-phenylethyl)
2,2,4,4-tetramethyl-1,3-oxazolidine-3-carboxylate

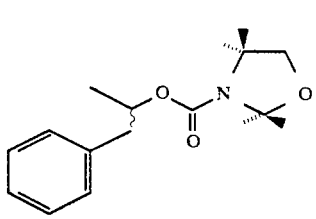

202 mg (35%) of the title compound were obtained analogously as a colorless oil from 403 mg (2.0 mmol) of the carbamate from Example 10 of the formula II, 325 mg (2.8 mmol) of TMEDA instead of (−)-sparteine, 2.8 mmol of sec-butyllithium and 460 mg (2.7 mmol) of benzyl bromide after working up and purification on silica gel (ether/pentane 1:7).

Example 9 of the formula I':

(S)-(−)-(1-Trimethylsilylethyl)
2,2,4,4-tetramethyl-1,3-oxazolidine-3-carboxylate

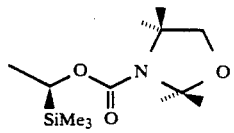

161 mg (59%) of the title compound were obtained analogously as a colorless oil from 200 mg (1.0 mmol) of the carbamate from Example 10 of the formula II, 340 mg (1.4 mmol) of (−)-sparteine, 1.4 mmol of sec-butyllithium and 217 mg (1.5 mmol) of trimethylsilyl chloride after working up and purification on silica gel (ether/pentane 1:12). $R_F=0.75$ (silica gel, ether/pentane 1:1), $[\alpha]_D^{19} = -26.6$ (c=1.66, $CH_2Cl_2$).

Example 10 of the formula I':

rac-(1-Trimethylsilylethyl)
2,2,4,4-tetramethyl-1,3-oxazolidine-3-carboxylate

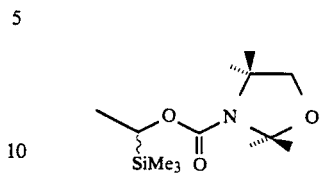

300 mg (55%) of the title compound were obtained analogously as a colorless oil using 402 mg (2.0 mmol) of the carbamate from Example 10 of the formula II, 325 mg (2.8 mmol) of TMEDA instead of (−)-sparteine, 2.8 mmol of sec-butyllithium and 434 mg (3.0 mmol) of trimethylsilyl chloride after working up and purification on silica gel (ether/pentane 1:12).

Example 11 of the formula I':

(S)-(+)-(1-Tributylstannylethyl)
2,2,4,4-tetramethyl-1,3-oxazolidine-3-carboxylate

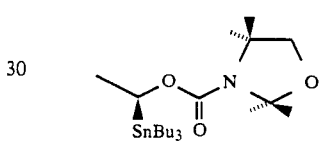

3.24 g (66%) of the title compound were obtained analogously as a colorless oil from 2.02 g (10.0 mmol) of the carbamate from Example 10 of the formula II, 3.40 g (14.0 mmol) of (−)-sparteine, 14.0 mmol of sec-butyllithium and 5.22 g (16.04 mmol) of tributylstannyl chloride after working up and purification on silica gel (ether/pentane 1:20). $R_F=0.74$ (silica gel, ether/pentane 1:4), $[\alpha]_D^{18} = +19.1$ (c=2.03, $CH_2Cl_2$).

Example 12 of the formula I':

rac-(1-Tributylstannylethyl)
2,2,4,4-tetramethyl-1,3-oxazolidine-3-carboxylate

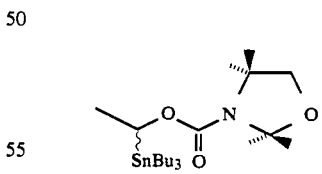

5.20 g (53% based on tributylstannyl chloride) of the title compound were obtained analogously as a colorless oil from 8.06 g (39.9 mmol) of the carbamate from Example 10 of the formula II, 6.74 g (58.1 mmol) of TMEDA instead of (−)-sparteine, 59.0 mmol of sec-butyllithium and 6.52 g (20.0 mmol) of tributylstannyl chloride after working up and purification on silica gel (ether/pentane 1:20).

Example 13 of the formula I':

(R)-(+)-(2-Hydroxy-1,2-dimethylpropyl) 2,2,4,4-tetramethyl-1,3-oxazolidine-3-carboxylate

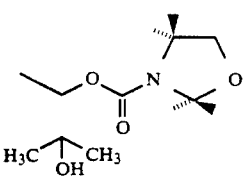

201 mg (1.0 mmol) of the carbamate from Example 10 of the formula II, 340 mg (1.0 mmol) of (−)-sparteine and 1.4 mmol of sec-butyllithium were reacted with one another analogously to Example 1 of the formula I'. 261 mg of lithium bromide (3.0 mmol), dissolved in 1 ml of ether and 1 ml of THF, were then added dropwise, the mixture was stirred at −78° C. for 5 min and 174 mg (3.0 mmol) of acetone, dissolved in 2 ml of ether, were then added. The reaction mixture was stirred for an additional 2½ hours at −78° C. and then quenched with 0.2 ml of glacial acetic acid. After warming to room temperature, working up and purification on silica gel (ether/pentane 1:1), 128 mg (49%) of the title compound were obtained as a colorless solid. $R_F=0.19$ (silica gel, ether/pentane 1:1), $[\alpha]_{365}^{21}=+23.5$ (c=1.22, $CH_2Cl_2$), m.p.: 53° C. (from the melt).

Example 14 of the formula I':

rac-(2-Hydroxy-1,2-dimethylpropyl) 2,2,4,4-tetramethyl-1,3-oxazolidine-3-carboxylate

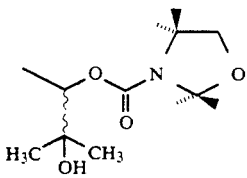

Analogously to Example 13 of the formula I', but without addition of lithium bromide, 348 mg (67%) of the title compound were obtained as a colorless solid using 403 mg (2.0 mmol) of the carbamate from Example 10 of the formula II, 325 mg (2.8 mmol) of TMEDA instead of (−)-sparteine, 2.8 mmol of sec-butyllithium and 174 mg (3.0 mmol) of acetone. M.p.: 70° C. (from the melt).

Example 15 of the formula I':

(R)-(+)-(1-Methyl-2-hydroxyethyl) 2,2,4,4-tetramethyl-1,3-oxazolidine-3-carboxylate

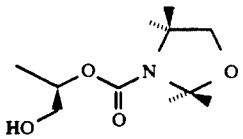

Analogously to Example 1 of the formula I', 359 mg (39%) of the title compound were obtained as a colorless oil from 806 mg (4.0 mmol) of the carbamate from Example 10 of the formula II, 1.36 g (5.8 mmol) of (−)-sparteine, 5.8 mmol of sec-butyllithium and 930 mg of solid paraformaldehyde, dried in a high vacuum, after working up and purification on silica gel (ether/pentane 1:1). $R_F=0.12$ (silica gel, ether/pentane 1:1), $[\alpha]_{365}^{19}=+30.5$ (c=1.27, $CH_2Cl_2$).

Example 16 of the formula I':

Methyl (R)-(−)-2-[(3,3-dimethyl-1-oxa-4-azaspiro[4.4]non-4-ylcarbonyl)oxy]octanoate

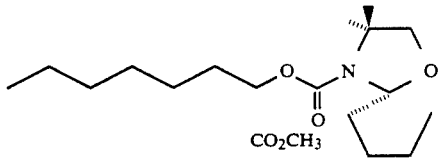

645 mg (90%) of the title compound were obtained analogously as a colorless oil of >95% ee from 598 mg (2.0 mmol) of the carbamate from Example 2 of the formula II, 680 mg of (−)-sparteine and 2.8 mmol of sec-butyllithium after passing excess carbon dioxide through the solution of the organolithium compound at −78° C., after working up and after subsequent methylation of the crude product with diazomethane in ether and subsequent column chromatography on silica gel (ether/pentane 1:4). $R_F=0.59$ (silica gel, ether/pentane 1:1), $[\alpha]_D^{16}=-11.6$ (c=1.60, $CH_2Cl_2$).

Example 17 of the formula I':

Methyl rac-2-[(3,3-dimethyl-1-oxa-4-azaspiro[4.4]non-4-ylcarbonyl)oxy]octanoate

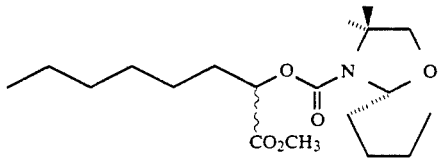

661 mg (95%) of the title compound were obtained analogously as a colorless oil from 590 mg (2.0 mmol) of the carbamate from Example 2 of the formula II, 325 mg (2.8 mmol, of TMEDA instead of (−)-sparteine and 2.8 mmol of sec-butyllithium.

Example 18 of the formula I':

Methyl (R)-(−)-2-[(2,2,4,4-tetramethyl-1,3-oxazolidine-3-ylcarbonyl)oxy]octanoate

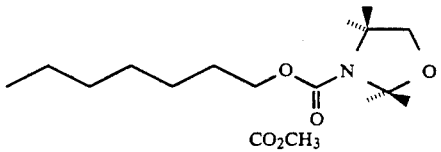

520 mg (79%) of the title compound were obtained analogously as a colorless oil of >95% ee from 543 mg (2.0 mmol) of the carbamate from Example 1 of the formula II, 680 mg (2.8 mmol) of (−)-sparteine and 2.8 mmol of sec-butyllithium after carboxylation, methylation and purification of the crude product on silica gel (ether/pentane 1:4). $R_F=0.51$ (silica gel, ether/pentane 1:1), $[\alpha]_D^{18}=-13.0$ (c=1.22, $CH_2Cl_2$).

Example 19 of the formula I':

Methyl rac-2-[(2,2,4,4-tetramethyl-1,3-oxazolidine-3-ylcarbonyl)oxy]octanoate

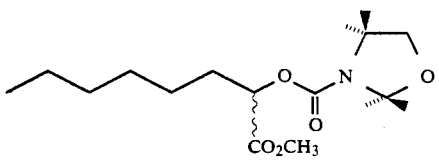

560 mg (85%) of the title compound were obtained analogously as a colorless oil from 543 mg (2.0 mmol) of the carbamate from Example 1 of the formula II, 325 mg (2.8 mmol) of TMEDA instead of (−)-sparteine and 2.8 mmol of sec-butyllithium.

Example 20 of the formula I':

(S)-(−)-[2-(N,N-Dibenzylamino)-1-methylethyl] 2,2,4,4-tetramethyl-1,3-oxazolidine-3-carboxylate

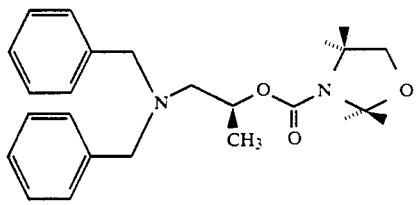

703 mg (3.0 mmol) of (−)-sparteine were initially introduced into 6 ml of anhydrous ether and mixed at −78° C. with 2.17 ml (3.0 mmol) of sec-butyllithium (1.4M in cyclohexane/isopentane). After stirring at this temperature for 10 min, 396 mg (1.0 mmol) of the carbamate from Example 5 of the formula II, dissolved in 2 ml of ether, were injected; the solution changed color to orange during the course of this. After a metalation time of 3 hours, 187 μl (3.0 mmol) of methyl iodide were added. The reaction mixture was warmed to room temperature overnight and hydrolyzed with 3 ml of water. After separation of the phases, the aqueous phase was washed a further three times with 5 ml of ether each time. The combined organic phases were dried over magnesium sulphate and freed of solvent in vacuo. After flash chromatography on silica gel, 301 mg (73%) of the title compound were obtained as colorless crystals. $R_F=0.61$ (silica gel, ether/pentane=1:1), m.p.: 117° C., $[\alpha]_{20}^D=-35.7$; $[\alpha]_{365}^{20}=-102.9$ c=1.0, $CHCl_3$).

Example 21 of the formula I':

rac-[2-(N,N-Dibenzylamino)-1-methylethyl) 2,2,4,4-tetramethyl-1,3-oxazolidine-3-carboxylate

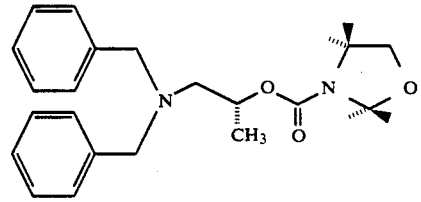

308 mg (75%) of the title compound were obtained analogously as a colorless solid from 396 mg (1.0 mmol) of the carbamate from Example 5 of the formula II using 2.17 ml (3.0 mmol) of sec-butyllithium, 446 μl (3.0 mmol) of tetramethylethylenediamine instead of (−)-sparteine and 187 μl (3.0 mmol) of methyl iodide.

Example 22 of the formula I':

(S)-(+)-[2-(N,N-Dibenzylamino)-1-trimethylsilylethyl] 2,2,4,4-tetramethyl-1,3-oxazolidine-3-carboxylate

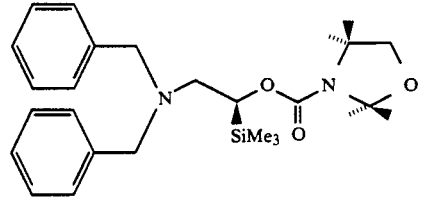

328 mg (70%) of the title compound were obtained analogously as a colorless oil from 396 mg (1.0 mmol) of the carbamate from Example 5 of the formula II and 378 μl (3.0 mmol) of trimethylsilyl chloride. $R_F=0.68$ (silica gel, ether/pentane=1:1), $[\alpha]_{20}^D=+6.2$; $[\alpha]_{365}^{20}=+22.2$ (c=1.5, $CHCl_3$).

Example 23 of the formula I':

rac-[2-(N,N-Dibenzylamino)-1-trimethylsilylethyl] 2,2,4,4-tetramethyl-1,3-oxazolidine-3-carboxylate

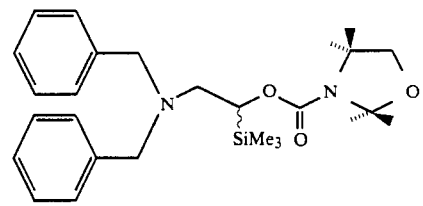

375 mg (80%) of the title compound were obtained analogously as a colorless oil in the reaction of 396 mg (1.0 mmol) of the carbamate from Example 5 of the formula II, 3.0 mmol of sec-butyllithium, 446 μl of TMEDA and 378 μl (3.0 mmol) of trimethylsilyl chloride.

Example 24 of the formula I':

(S)-(+)-[2-(N,N-Dibenzylamino)-1-tributylstannylethyl] 2,2,4,4-tetramethyl-1,3-oxazolidine-3-carboxylate

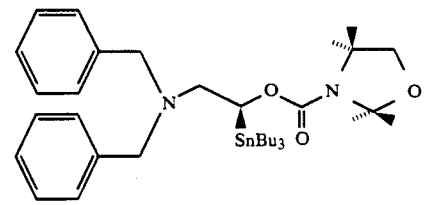

480 mg (70%) of the title compound were obtained analogously as a colorless oil from 396 mg (1.0 mmol) of the carbamate from Example 5 of the formula II and 865 μl (3.0 mmol) of tributylstannyl chloride. $R_F=0.73$ (silica gel, ether/pentane=1:1), $[\alpha]_{20}^D=+28.4$; $[\alpha]_{365}^{20}=+99.3$ (c=1.3, $CHCl_3$).

Example 25 of the formula I':

rac-[2-(N,N-Dibenzylamino)-1-tributylstannylethyl] 2,2,4,4-tetramethyl-1,3-oxazolidine-3-carboxylate

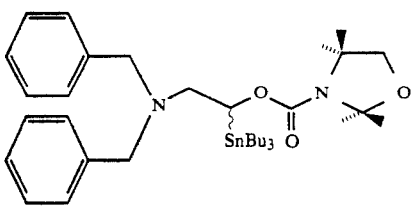

466 mg (68%) of the title compound were obtained analogously as a colorless oil in the reaction of 396 mg (1.0 mmol) of the carbamate from Example 5 of the formula II, 3.0 mmol of sec-butyllithium, 446 µl of TMEDA and 865 µl (3.0 mmol) of tributylstannyl chloride.

Example 26 of the formula I':

Methyl (R)-(−)-3-(N,N-dibenzylamino)-2-[(2,2,4,4-tetramethyl-1,3-oxazolidine-3-carbonyl)oxy]propanoate

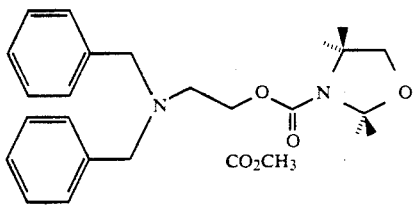

After the 3-hour metalation of 396 mg (1.0 mmol) of the carbamate from Example 5 of the formula II with n-BuLi as described hereinabove under General Working Procedure II, carbon dioxide was passed in for 0.5 h and the mixture was warmed to room temperature; working up was carried out using 5 ml of 2N hydrochloric acid. The organic phase was separated off and the aqueous phase was extracted three times with 5 ml of ether each time. The combined organic phases were dried over magnesium sulphate and concentrated in vacuo. The crude product was taken up in 5 ml of ether and treated with diazomethane until a yellow coloration persisted; excess diazomethane was destroyed with 1 g of silica gel. Filtering off, concentration in vacuo and flash chromatography gave 254 mg (56% over 2 steps) of the title compound as a colorless oil. $R_F=0.46$ (silica gel, ether/pentane=1:1), $[\alpha]_{20}{}^D=-7.8$; (c=0.8, CHCl$_3$)

Example 27 of the formula I':

(S)-(+)-[3-(N,N-Dimethylamino)-1-methylpropyl] 2,2,4,4-tetramethyl-1,3-oxazolidine-3-carboxylate

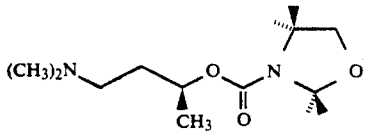

249 mg (92%) of the title compound were obtained, analogously to Example 20 of the formula I', as a colorless oil having a rotation $[\alpha]_D{}^{20}=+1.31$ (c=1.1, acetone) from 258 mg (1.0 mmol) of the carbamate from Example 6 of the formula II, 398 mg (1.7 mmol) of (−)-sparteine, 1.6 mmol of sec-butyllithium and 426 mg (3.0 mmol) of methyl iodide after a 4 h metalation time and purification of the crude product on alumina (ether).

Example 28 of the formula I':

rac-[3-(N,N-Dimethylamino)-1-methylpropyl] 2,2,4,4-tetramethyl-1,3-oxazolidine-3-carboxylate

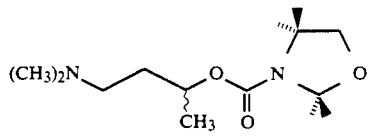

188 mg (69%) of the title compound were obtained analogously as a colorless oil from 1.6 mmol of sec-buLi, 258 mg (1.0 mmol) of the carbamate from Example 6 of the formula II and 426 mg (3.0 mmol) of methyl iodide after a 4 h metalation time and purification of the crude product on alumina (ether). $R_F=0.45$ (alumina, ethyl acetate).

Example 29 of the formula I':

(S)-(+)-[3-(N,N-Dibenzylamino)-1-methylpropyl] 2,2,4,4-tetramethyl-1,3-oxazolidine-3-carboxylate

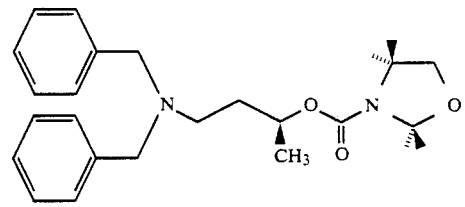

348 mg (82%) of the title compound were obtained analogously as a colorless oil having a rotation $[\alpha]_D{}^{20}=+21.5$ (c=1.0, acetone) from 410 mg (1.0 mmol) of the carbamate from Example 7 of the formula II, 469 mg (2.0 mmol) of (−)-sparteine, 1.9 mmol of sec-butyllithium and 426 mg (3.0 mmol) of methyl iodide after a 2.5 h metalation time and purification of the crude product on silica gel (ether/pentane 1:4). $R_F=0.44$ (silica gel, ether/pentane 1:2).

Example 30 of the formula I':

rac-[3-(N,N-Dibenzylamino)-1-methylpropyl] 2,2,4,4-tetramethyl-1,3-oxazolidine-3-carboxylate

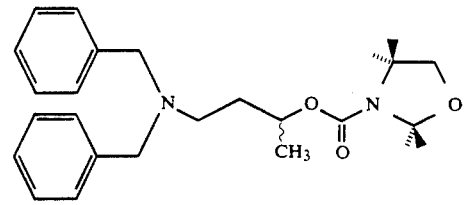

338 mg (80%) of the title compound were obtained analogously as a colorless oil from 410 mg (1.0 mmol) of the carbamate from Example 7 of the formula II, 232 mg (2.0 mmol) of TMEDA instead of (−)-sparteine, 1.9 mmol of sec-butyllithium and 426 mg (3.0 mmol) of methyl iodide after a 1 h metalation time and purification of the crude product on silica gel (ether/pentane 1:2).

Example 31 of the formula I':

(R)-(+)-[1-Benzyl-3-(N,N-dibenzylamino)-propyl] 2,2,4,4-tetramethyl-1,3-oxazolidine-3-carboxylate

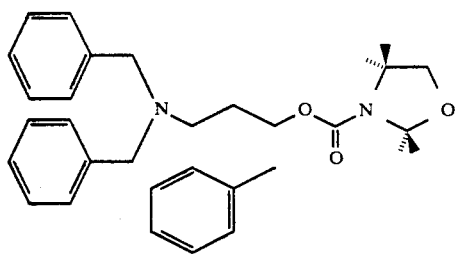

225 mg (45%) of the title compound were obtained, analogously to Example 33 of the formula I', as a colorless oil having a rotation $[\alpha]_D^{20} = +1.7$ (c=0.8, acetone) from 410 mg (1.0 mmol) of the carbamate from Example 7 of the formula II, 469 mg (2.0 mmol) of (−)-sparteine, 1.8 mmol of sec-butyllithium and 513 mg (3.0 mmol) of benzyl bromide after a 3 h metalation time and purification of the crude product on silica gel (ether/pentane 1:4). $R_F=0.51$ (silica gel, ether/pentane 1:2).

Example 32 of the formula I':

rac-[1-Benzyl-3-(N,N-dibenzylamino)-propyl] 2,2,4,4-tetramethyl-1,3-oxazolidine-3-carboxylate

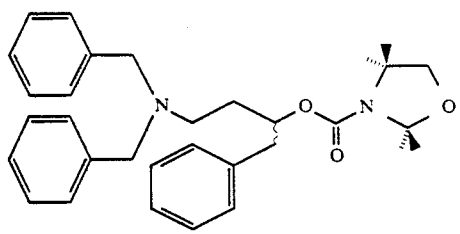

201 mg (40%) of the title compound were obtained analogously as a colourless oil from 410 mg (1.0 mmol) of the carbamate from Example 7 of the formula II, 233 mg (2.0 mmol) of TMEDA instead of (−)-sparteine, 1.8 mmol of sec-butyllithium and 513 mg (3.0 mmol) of benzyl bromide after a 3 h metalation time and purification of the crude product on silica gel (ether/pentane 1:4).

Example 33 of the formula I':

(S)-(+)-[3-(N,N-Dimethylamino)-1-trimethylsilylpropyl] 2,2,4,4-tetramethyl-1,3-oxazolidine-3-carboxylate

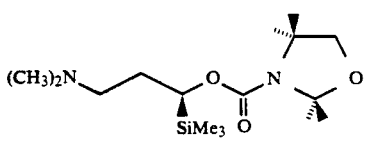

A mixture of 8 ml of anhydrous ether and 469 mg (2.0 mmol) of (−)-sparteine was cooled to −78° C. and treated slowly with 1.8 mmol of sec-butyllithium solution (in cyclohexane/isopentane). After stirring for 10 min, 258 mg (1 mmol) of the carbamate from Example 6 of the formula II, dissolved in 2 ml of ether, were added slowly. The reaction mixture was stirred at −78° C. for 4 h and 326 mg (3.0 mmol) of trimethylsilyl chloride were then added. After a reaction time of 2 h, the mixture was slowly brought to room temperature and poured into 10 ml of water for working up. The organic phase was separated off, the aqueous phase was washed a further four times with 10 ml of ether each time, the combined organic phases were dried over sodium sulphate and the solvent was removed in vacuo. The crude product was purified on alumina (ether). 216 mg (66%) of the title compound were obtained as a colorless oil having a rotation $[\alpha]_D^{20} = +1.02$ (c=1.0, acetone).

Example 34 of the formula I':

rac-[3-(N,N-Dimethylamino)-1-trimethylsilylpropyl] 2,2,4,4-tetramethyl-1,3-oxazolidine-3-carboxylate

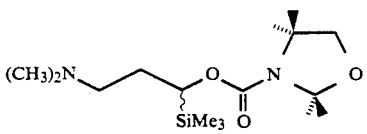

Analogously, but without addition of (−)-sparteine or TMEDA, 294 mg (89%) of the title compound were obtained as a colorless oil from 258 mg (1.0 mmol) of the carbamate from Example 6 of the formula II, 1.8 mmol of sec-butyllithium and 326 mg of trimethylsilyl chloride. $R_F=0.53$ (alumina, ethyl acetate).

Example 35 of the formula I':

(S)-(+)-[3-(N,N-Dibenzylamino)-1-trimethylsilylpropyl] 2,2,4,4-tetramethyl-1,3-oxazolidine-3-carboxylate

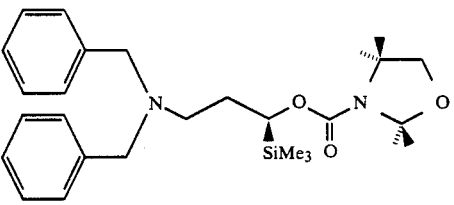

373 mg (77%) of the title compound were obtained analogously as a colorless oil having a rotation $[\alpha]_D^{20} = +5.32$ (c=1.1, acetone) from 410 mg (1.0 mmol) of the carbamate from Example 7 of the formula II, 469 mg (2.0 mmol) of (−)-sparteine, 1.9 mmol of sec-butyllithium and 326 mg (3.0 mmol) of trimethylsilyl chloride after a 2.5 h metalation time and purification of the crude product on silica gel (ether/pentane 1:4). $R_F=0.53$ (silica gel, ether/pentane 1:2).

Example 36 of the formula I':

rac-[3-(N,N-Dibenzylamino)-1-trimethylsilylpropyl] 2,2,4,4-tetramethyl-1,3-oxazolidine-3-carboxylate

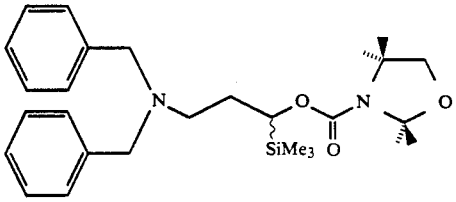

Analogously, but without addition of (−)-sparteine or TMEDA, 411 mg (85%) of the title compound were obtained as a colorless oil from 410 mg (1.0 mmol) of the carbamate (2.0 mmol) of TMEDA instead of (−)-sparteine, 1.9 mmol of sec-butyllithium and 326 mg (3.0 mmol) of trimethylsilyl chloride after a 1 h metalation time and purification of the crude product on silica gel (ether/pentane 1:4).

Example 37 of the formula I':

(S)-(+)-[3-(N,N-Dimethylamino)-1-trimethylstannyl-propyl] 2,2,4,4-tetramethyl-1,3-oxazolidine-3-carboxylate

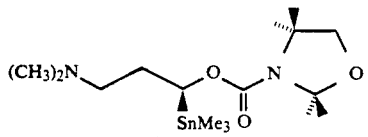

213 mg (51%) of the title compound were obtained analogously as a colorless oil having a rotation $[\alpha]_D^{20}=+2.12$ (c=1.1, acetone) from 258 mg (1.0 mmol) of the carbamate from Example 6 of the formula II, 398 mg (1.7 mmol) of (−)-sparteine, 1.5 mmol of sec-butyllithium and 598 mg (3.0 mmol) of trimethylstannyl chloride after a 4 h metalation time and purification of the crude product on alumina (ether).

Example 38 of the formula I':

rac-[3-(N,N-Dimethylamino)-1-trimethylstannylpropyl] 2,2,4,4-tetramethyl-1,3-oxazolidine-3-carboxylate

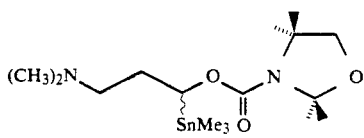

Analogously, but without addition of (−)-sparteine or TMEDA, 796 mg (95%) of the title compound were obtained as a colorless oil from 258 mg (1.0 mmol) of the carbamate from Example 6 of the formula II, 1.5 mmol of sec-buLi and 598 mg (3.0 mmol) of trimethylstannyl chloride after a 4 h metalation time and purification of the crude product on alumina (ether). $R_F=0.66$ (alumina, ethyl acetate).

Example 39 of the formula I':

(S)-(+)-[3-(N,N-Dibenzylamino)-1-trimethylstannyl-propyl] 2,2,4,4-tetramethyl-1,3-oxazolidine-3-carboxylate

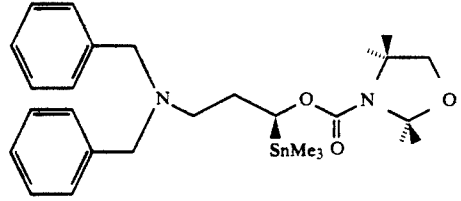

530 mg (93%) of the title compound were obtained analogously as a colorless oil having a rotation $[\alpha]_D^{20}=+31.9$ (c=1.1, acetone) from 410 mg (1.0 mmol) of the carbamate from Example 7 of the formula II, 469 mg (2.0 mmol) of (−)-sparteine, 1.8 mmol of sec-butyllithium and 598 mg (3.0 mmol) of trimethylstannyl chloride after a 4.5 h metalation time and purification of the crude product on silica gel (ether/pentane 1:4). $R_F=0.63$ (silica gel, ether/pentane 1:2).

Example 40 of the formula I':

rac-[3-(N,N-Dibenzylamino)-1-trimethylstannylpropyl] 2,2,4,4-tetramethyl-1,3-oxazolidine-3-carboxylate

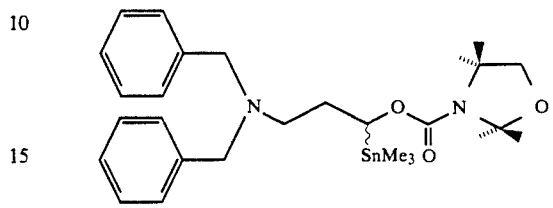

388 mg (67%) of the title compound were obtained analogously as a colorless oil from 410 mg (1.0 mmol) of the carbamate from Example 7 of the formula II, 232 mg (2.0 mmol) of TMEDA instead of (−)-sparteine, 1.8 mmol of sec-butyllithium and 598 mg (3.0 mmol) of trimethylstannyl chloride after a 1 h metalation time and purification of the crude product on silica gel (ether/pentane 1:4).

Example 41 of the formula I':

(R)-(+)-[3-(N,N-Dibenzylamino)-2-(2-methyl-2-hydroxyethyl)] 2,2,4,4-tetramethyl-,3-oxazolidine-3-carboxylate

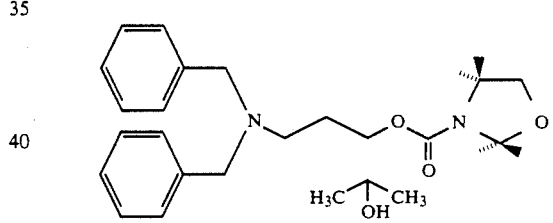

A mixture of 8 ml of anhydrous ether and 186 mg (1.6 mmol) of TMEDA was cooled to −78° C. and treated slowly with 1.4 mmol of sec-butyllithium solution (in cyclohexane/isopentane). After stirring for 10 min, 460 mg (1.0 mmol) of the carbamate from Example 39 of the formula I', dissolved in 2 ml of ether, were slowly injected. The reaction mixture was stirred at −78° C. for 2.5 h and 174 mg (3.0 mmol) of acetone were then added. After a reaction time of 4 hours at −78° C., the mixture was slowly brought to room temperature and poured into 10 ml of water for working up. The organic phase was separated off, the aqueous phase was extracted four times with 10 ml of ether each time, the combined organic phases were dried over sodium sulphate and the solvent was removed in vacuo. After purification of the crude product on silica gel (ether/pentane 1:1), 188 mg (50%) of the title compound were obtained as a colorless oil having a rotation $[\alpha]_D^{20}=+13.1$ (c=0.9, acetone).

Example 42 of the formula I':

rac-[3-(N,N-Dibenzylamino)-2-(2-methyl-2-hydroxyethyl)]
2,2,4,4-tetramethyl-1,3-oxazolidine-3-carboxylate

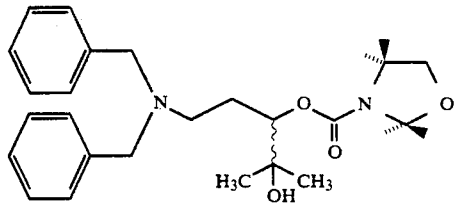

253 mg (55%) of the title compound were obtained analogously to Example 33 of the formula I'as a colorless oil from 410 mg (1.0 mmol) of the carbamate from Example 7 of the formula II, 232 mg (2.0 mmol) of TMEDA instead of (−)-sparteine, 1.8 mmol of sec-butyllithium and 174 mg (3.0 mmol) of acetone after a 3 h metalation time and purification of the crude product on silica gel (ether/pentane 1:4). $R_F=0.25$ (silica gel, ether/pentane 1:1).

Example 43 of the formula I':

Methyl
(R)-[4-(N,N-dibenzylamino)-2-(2,2,4,4-tetramethyl-1,3-oxazolidine-3-ylcarbonyl)oxy]butanoate

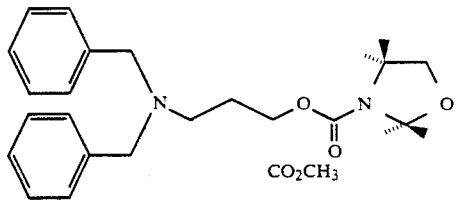

The carboxylic acid, which after working up was freed from the solvent in vacuo, was obtained analogously from 410 mg (1.0 mmol) of the carbamate from Example 7 of the formula II, 469 mg (2.0 mmol) of (−)-sparteine and 1.9 mmol of sec-butyllithium, after gaseous carbon dioxide has been introduced after a 4.5 h metalation time. The carboxylic acid, without purification, was treated with anhydrous ether and, until a yellow coloration of the mixture persisted, with a solution of diazomethane in ether. It was stirred at room temperature for 2 h, the excess diazomethane was destroyed with silica gel and the solvent was removed. After purification of the crude product on silica gel (ether/pentane 1:2), 256 mg (55%) of the title compound were obtained as a colorless oil having a rotation $[\alpha]_D^{20}=+10.9$ (c=1.0, acetone). $R_F=0.29$ (silica gel, ether/pentane 1:2).

Example 44 of the formula I':

Methyl
rac-[4-(N,N-dibenzylamino)-2-(2,2,4,4-tetramethyl-1,3-oxazolidine-3-ylcarbonyl)oxy]butanoate

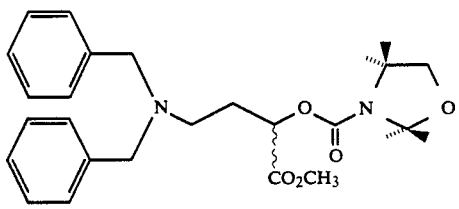

358 mg (77%) of the title compound were obtained analogously as a colorless oil using 410 mg (1.0 mmol) of the carbamate from Example 7 of the formula II, 232 mg (2.0 mmol) of TMEDA instead of (−)-sparteine and 1.9 mmol of sec-butyllithium after the metalation of the crude product and purification of the crude product on silica gel (ether/pentane 1:2).

Example 45 of the formula I':

(S)-(+)-(4-Methoxy-1-methylbutyl)
3,3-dimethyl-1-oxa-4-azaspiro[4.5]decane-4-carboxylate

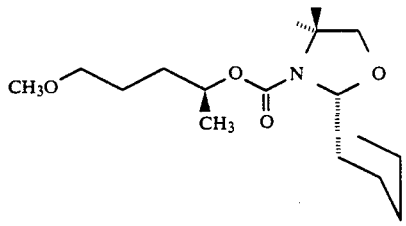

Analogously to Example 1 of the formula I', 741 mg (79%) of the title compound of 97% ee were obtained as a colorless oil from 897 mg (3.0 mmol) of the carbamate from Example 9 of the formula II, 692 mg (3.0 mmol) of (−)-sparteine, 2.9 mmol of sec-butyllithium and 684 mg (4.8 mmol) of methyl iodide after working up and purification on silica gel (ether/pentane 1:4). $R_F=0.47$ (silica gel, ether/pentane 1:1), $[\alpha]_D^{20}=+9.7$ (c=0.9, CH$_2$Cl$_2$).

Example 46 of the formula I':

rac-(4-Methoxy-1-methylbutyl)
3,3-dimethyl-1-oxa-4-azaspiro[4.5]decane-4-carboxylate

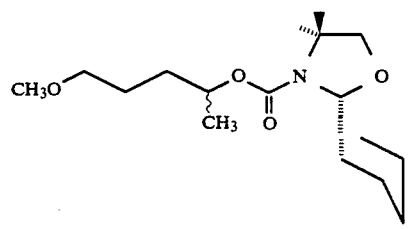

631 mg (67%) of the title compound were obtained analogously as a colorless oil from 897 mg (3.0 mmol) of the carbamate from Example 9 of the formula II, 501 mg (4.3 mmol) of TMEDA instead of (−)-sparteine, 2.9 mmol of sec-butyllithium and 684 mg (4.8 mmol) of methyl iodide after working up and purification on silica gel (ether/pentane 1:4).

Example 47 of the formula I':

(R)-(−)-[4-Methoxy-1-(phenylmethyl)butyl] 3,3-dimethyl-1-oxa-4-azaspiro[4.5]decane-4-carboxylate

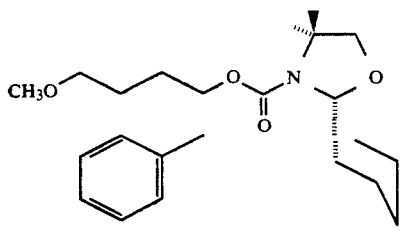

353 mg (45%) of the title compound of 39% ee were obtained analogously as a colorless oil from 605 mg (2.0 mmol) of the carbamate from Example 9 of the formula II, 692 mg (3.0 mmol) of (−)-sparteine, 2.9 mmol of sec-butyllithium and 576 mg (3.4 mmol) of benzyl bromide after working up and purification on silica gel (ether/pentane 1:3). $R_F=0.46$ (silica gel, ether/pentane 1:1), $[\alpha]_D^{24}=-2.5$ (c=0.9, CH$_2$Cl$_2$).

Example 48 of the formula I':

rac-[4-Methoxy-1-(phenylmethyl)butyl] 3,3-dimethyl-1-oxa-4-azaspiro[4.5]decane-4-carboxylate

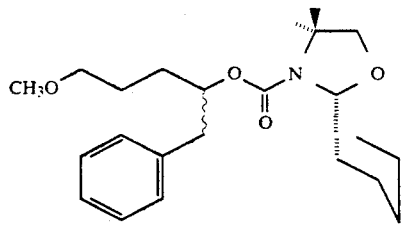

215 mg (27%) of the title compound were obtained analogously as a colorless oil from 603 mg (2.0 mmol) of the carbamate from Example 9 of the formula II, 342 mg (3.0 mmol) of TMEDA instead of (−)-sparteine, 2.9 mmol of sec-butyllithium and 576 mg (3.4 mmol) of benzyl bromide after working up and purification on silica gel (ether/pentane 1:3).

Example 49 of the formula I':

(R)-(+)-[4-Methoxy-1-(propen-2-yl)butyl] 3,3-dimethyl-1-oxa-4-azaspiro[4.5]decane-4-carboxylate

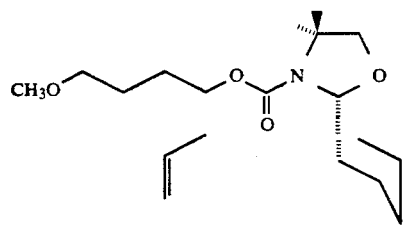

430 mg (63%) of the title compound were obtained analogously as a colorless oil from 601 mg (2.0 mmol) of the carbamate from Example 9 of the formula II, 692 mg (3.0 mmol) of (−)-sparteine, 2.9 mmol of sec-butyllithium and 429 mg (3.5 mmol) of allyl bromide after working up and purification on silica gel (ether/pentane 1:3). $R_F=0.50$ (silica gel, ether/pentane 1:1), $[\alpha]_D^{18}=+2.5$ (c=3.2, CH$_2$Cl$_2$).

Example 50 of the formula I':

rac-[4-Methoxy-1-(propen-2-yl)butyl] 3,3-dimethyl-1-oxa-4-azaspiro[4.5]decane-4-carboxylate

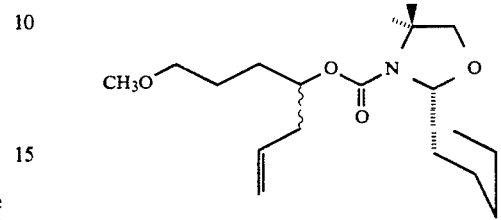

433 mg (65%) of the title compound were obtained analogously as a colorless oil from 593 mg (2.0 mmol) of the carbamate from Example 9 of the formula II, 338 mg (2.9 mmol) of TMEDA instead of (−)-sparteine, 2.9 mmol of sec-butyllithium and 429 mg (3.5 mmol) of allyl bromide after working up and purification on silica gel (ether/pentane 1:3).

Example 51 of the formula I':

(S)-(+)-[4-Methoxy-1-(trimethylsilyl)butyl] 3,3-dimethyl-1-oxa-4-azaspiro[4.5]decane-4-carboxylate

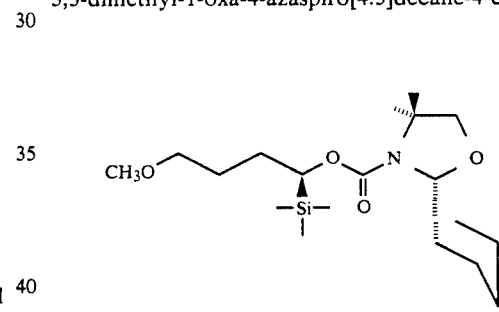

691 mg (62%) of the title compound were obtained analogously as a colorless oil of 92% ee from 895 mg (3.0 mmol) of the carbamate from Example 9 of the formula II, 692 mg (3.0 mmol) of (−)-sparteine, 2.9 mmol of sec-butyllithium and 516 mg (4.8 mmol) of trimethylsilyl chloride after working up and purification on silica gel (ether/pentane 1:4). $R_F=0.52$ (silica gel, ether/pentane 1:1), $[\alpha]_D^{22}=+2.6$ (c=1.0, CH$_2$Cl$_2$).

Example 52 of the formula I':

rac-[4-Methoxy-1-(trimethylsilyl)butyl] 3,3-dimethyl-1-oxa-4-azaspiro[4.5]decane-4-carboxylate

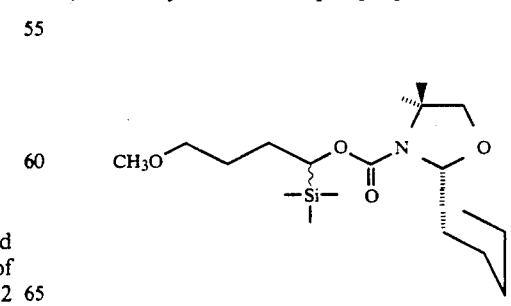

598 mg (80%) of the title compound were obtained analogously as a colorless oil from 598 mg (2.0 mmol) of the carbamate from Example 9 of the formula II, 332 mg (2.9 mmol) of TMEDA instead of (−)-sparteine, 2.9 mmol of sec-butyllithium and 516 mg (4.8 mmol) of trimethylsilyl chloride after working up and purification on silica gel (ether/pentane 1:4).

Example 53 of the formula I′:

(S)-(+)-[4-Methoxy-1-(trimethylstannyl)butyl] 3,3-dimethyl-1-oxa-4-azaspiro[4.5]decane-4-carboxylate

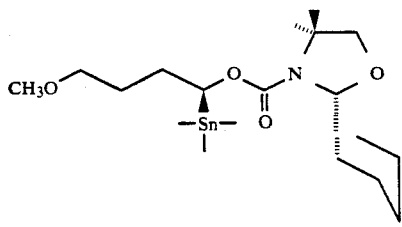

652 mg (70%) of the title compound are obtained analogously as a colorless oil of >99.5% ee from 602 mg (2.0 mmol) of the carbamate from Example 9 of the formula II, 692 mg (3.0 mmol) of (−)-sparteine, 2.9 mmol of sec-butyllithium and 620 mg (3.1 mmol) of trimethylstannyl chloride after working up and purification on silica gel (ether/pentane 1:5). $R_F=0.61$ (silica gel, ether/pentane 1:1), $[\alpha]_D^{20}=+35.5$ (c=1.0, $CH_2Cl_2$).

Example 54 of the formula I′:

rac-[4-Methoxy-1-(trimethylstannyl)butyl] 3,3-dimethyl-1-oxa-4-azaspiro[4.5]decane-4-carboxylate

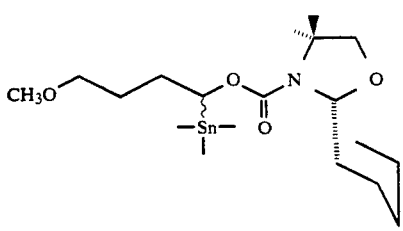

501 mg (54%) of the title compound were obtained analogously as a colorless oil from 600 mg (2.0 mmol) of the carbamate from Example 9 of the formula II, 330 mg (2.8 mmol) of TMEDA instead of (−)-sparteine, 2.9 mmol of sec-butyllithium and 620 mg (3.1 mmol) of trimethylstannyl chloride after working up and purification on silica gel (ether/pentane 1:5).

Example 55 of the formula I′:

Methyl (R)-(−)-2-[(3,3-dimethyl-1-oxa-4-azaspiro[4.5]dec-4-ylcarbonyl]oxy]-5-methoxypentanoate

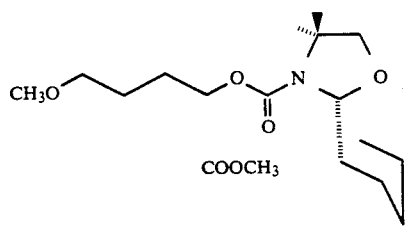

Analogously to Example 16 of the formula I′, 434 mg (61%) of the title compound were obtained as a colorless oil of >95% ee from 598 mg (2.0 mmol) of the carbamate from Example 9 of the formula II, 692 mg (3.0 mmol) of (−)-sparteine and 2.9 mmol of sec-butyllithium after working up and purification on silica gel (ether/pentane 1:3). $R_F=0.35$ (silica gel, ether/pentane 1:1), $[\alpha]_D^{20}=-13.0$ (c=1.8, $CH_2Cl_2$).

Example 56 of the formula I′:

Methyl rac-2-[(3,3-dimethyl-1-oxa-4-azaspiro[4.5]dec-4-ylcarbonyl]oxy]-5-methoxypentanoate

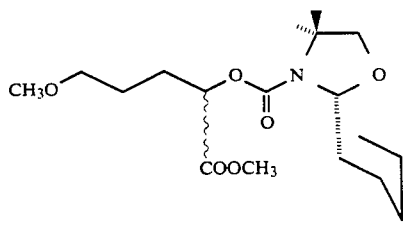

707 mg (51%) of the title compound were obtained analogously as a colorless oil from 1.20 g (4.0 mmol) of the carbamate from Example 9 of the formula II, 677 mg (5.8 mmol) of TMEDA instead of (−)-sparteine and 5.9 mmol of sec-butyllithium after working up and purification on silica gel (ether/pentane 1:3).

3. Deblocking of the OH function

Method A:

Example 1 of the formula I:

Methyl (R)-(−)-2-hydroxyoctanoate

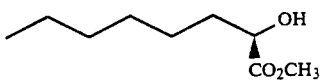

363 mg (1.1 mmol) of fh 47 were heated under reflux with 10 ml of 5N HCl for 24 hours, dark droplets forming. The reaction mixture was extracted three times with 20 ml of ether each time and the combined organic phases were dried over sodium sulphate. After removal of the solvent in vacuo, the solid residue was taken up in 10 ml of dry ether and treated with excess diazomethane in ether and stirred at room temperature for 3 hours. After destroying the excess diazomethane by means of a little silica gel, the solvent was removed in vacuo and the residue was chromatographed on silica gel (ether/- pentane 1:4). 152 mg (79%) of the title compound were obtained as a colorless oil. $R_F=0.39$ (silica gel, ether/pentane 1:1), $[\alpha]_D^{16}=-9.4$ (c=1.20, CHCl$_3$).

Method B:

Example 2 of the formula I:

(S)-2-Octanol

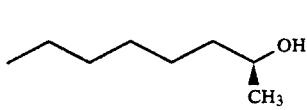

333 mg (1.1 mmol) of the carbamate from Example 2 of the formula I' were dissolved in 10 ml of methanol and heated under reflux with 0.05 ml of methanesulphonic acid for 16 hours. 0.5 g of barium hydroxide octahydrate were then added and the mixture was heated under reflux for a further 4 hours. The reaction mixture was poured into 10 ml of 2N HCl and extracted three times with 20 ml of ether each time. The combined organic phases were deacidified and dried over solid sodium hydrogen sulphate and sodium sulphate in the volume ratio 1:2. After the removal of the solvent in vacuo, the residue was purified on silica gel (ether/pentane 1:3). 124 mg (89%) of the title compound were obtained as a colorless oil of 95% ee. $R_F=0.38$ (silica gel, ether/pentane 1:1).

Example 3 of the formula I:

(S)-2-Octanol

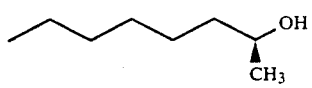

121 mg (93%) of the title compound of 95% ee were obtained analogously from 285 mg (1.0 mmol) of the carbamate from Example 1 of the formula I'.

Example 4 of the formula I:

(R)-Pent-4-en-2-ol

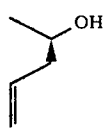

28 mg (33%) of the title compound were obtained analogously as a colorless liquid of 42% ee from 241 mg (1.0 mmol) of the carbamate from Example 4 of the formula I'. $R_F=0.32$ (silica gel, ether/pentane 1:1).

Example 5 of the formula I:

(R)-(−)-3-Phenyl-propan-2-ol

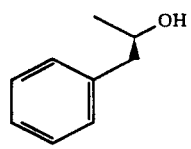

64 mg (76%) of the title compound were obtained analogously as a colorless liquid of 44% ee from 180 mg (0.62 mmol) of the carbamate from Example 7 of the formula I'. $R_F=0.33$ (ether/pentane 1:1), $[\alpha]_{365}^{23}=-32.3$ (c=1.90, ether).

Example 6 of the formula I:

rac-3-Phenyl-propan-2-ol

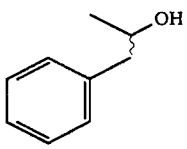

66 mg (83%) of the title compound were obtained analogously as a colorless liquid from 171 mg (0.59 mmol) of the carbamate from Example 8 of the formula I'.

Example 7 of the formula I:

(S)-(+)-3-(N,N-Dibenzylamino)-propan-2-ol

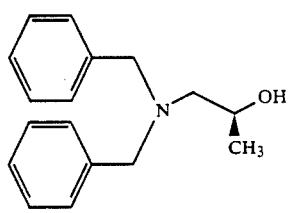

90 mg (71%) of the title compound were obtained analogously as a colorless oil from 205 mg (0.5 mmol) of the carbamate from Example 20 of the formula I' after separation by column chromatography on silica gel (ether/pentane 2:1). $R_F=0.36$ (silica gel, ether/pentane 1:1), $[\alpha]_D^{20}=+99.4$; $[\alpha]_{365}^{20}=+335.6$ (c=1.0, CHCl$_3$).

Example 8 of the formula I:

(S)-(+)-5-Methoxypentan-2-ol

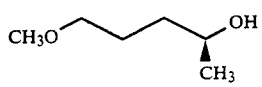

21 mg (58%) of the title compound were obtained analogously as a yellow oil of 97% ee from 98 mg (0.31 mmol) of the carbamate from Example 45 of the formula I' after separation by column chromatography on silica gel (ether/pentane 3:1). $R_F=0.09$ (silica gel, ether/pentane=1:1), $[\alpha]_D^{20}=+12.6$ (c=0.2, CH$_2$Cl$_2$).

Example 9 of the formula I:

(R)-(−)-5-Methoxy-1-phenylpentan-2-ol

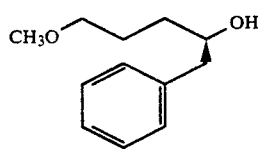

39 mg (38%) of the title compound were obtained analogously as a yellow oil of 39% ee from 206 mg (0.5 mmol) of the carbamate from Example 47 of the formula I' after separation by column chromatography on silica gel (ether/pentane 3:1). $R_F=0.16$ (silica gel, ether/pentane=1:1), $[\alpha]_D^{17}=-2.8$ (c=0.9, CH$_2$Cl$_2$).

Example 10 of the formula I:

(S)-(+)-4-Methoxy-1-trimethylsilylbutan-1-ol

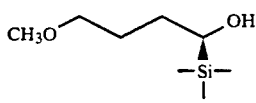

43 mg (75%) of the title compound were obtained analogously as a yellow oil of 92% ee from 119 mg (0.3 mmol) of the carbamate from Example 51 of the formula I' after separation by column chromatography on silica gel (ether/pentane 1:3). $R_F=0.16$ (silica gel, ether/pentane=1:1), $[\alpha]_D^{22}=+8.8$ (c=1.1, $CH_2Cl_2$).

Method C:

Example 11 of the formula I:

rac-2-Methylbutane-2,3-diol

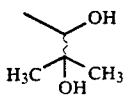

286 mg (1.1 mmol) of the carbamate from Example 14 of the formula I' were heated under reflux in 8 ml of anhydrous THF with 400 mg (10.5 mmol) of lithium aluminum hydride for 22 hours. The mixture was then allowed to cool to room temperature, 5 ml of THF and 0.6 ml of 30% sodium hydroxide solution were added dropwise and the reaction mixture was boiled under reflux for a further 60 min. After filtration through a little silica gel, the solvent was removed in vacuo and the residue was purified on silica gel (acetone/n-pentane 1:4). 114 mg (97%) of the title compound were obtained as a colorless oil. $R_F=0.42$ (silica gel, acetone/pentane 1:1).

Example 12 of the formula I:

(R)-2-Methylbutane-2,3-diol

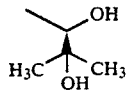

40 mg (78%) of the title compound were obtained analogously as a colorless liquid of >80% ee from 128 mg (0.49 mmol) of the carbamate from Example 13 of the formula I' $R_F=0.42$ (acetone/pentane 1:1).

Example 13 of the formula I:

(R)-(−)-Propane-1,2-diol

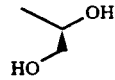

87 mg (76%) of the title compound were obtained analogously as a colorless liquid of >80% ee from 350 mg (1.5 mmol) of the carbamate from Example 15 of the formula I' $R_F=0.35$ (silica gel, acetone/pentane 1:1), $[\alpha]_{365}^{20}=-47.1$ (c=2.10, $CHCl_3$).

It will be understood that the specification examples are illustrative but not limitative of the present invention and that other embodiments within the spirit and scope of the invention will suggest themselves to those skilled in the art.

We claim:

1. A process for the preparation of a compound of the formula

in which

R$^1$ represents hydrogen or an electrofugic leaving group, or represents straight-chain or branched alkyl or alkenyl in each case having up to 10 carbon atoms which are optionally substituted by alkoxy having up to 6 carbon atoms, phenyl or by the group —NR$^3$R$^4$, in which R$^3$ and R$^4$ are identical or different and denote hydrogen, straight-chain or branched alkyl having up to 8 carbon atoms, phenyl or benzyl, R$^2$ represent hydrogen, or R$^1$ and R$^2$ together form a cyclopentyl ring and E represents straight-chain or branched alkyl or alkenyl in each case having up to 6 carbon atoms which are optionally monosubstituted or trisubstituted by identical or different substituents selected from the group consisting of hydroxyl, phenyl, cyclobutyl, cyclopentyl, cyclohexyl and a group of the formula —NR$^3$R$^4$, —HN—CO—OR$^5$, —SiR$^6$R$^7$R$^8$ or SnR$^{6'}$R$^{7'}$R$^{8'}$, and R$^5$ denotes straight-chain or branched alkyl having up to 6 carbon atoms, which is optionally substituted by phenyl, and R$^6$, R$^7$, R$^8$, R$^{6'}$, R$^{7'}$ and R$^{8'}$ are identical or different and denote straight-chain or branched alkyl, having up to 6 carbon atoms, or E represents cyclobutyl or cyclohexyl which is optionally substituted by hydroxyl, or represents carboxyl, methoxycarbonyl or a group of the formula —SiR$^6$R$^7$R$^8$ or SnR$^{6'}$R$^{7'}$R$^{8'}$ or R$^9$—CO, and R$^9$ - denotes hydrogen or straight-chain or branched alkyl or alkenyl in each case having up to 8 carbon atoms which is optionally monosubstituted to trisubstituted by phenyl or by the group of the formula —NH—CO—OR$^5$, which comprises deprotonating a carbamate of the formula

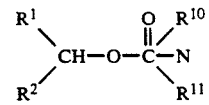

in which

R$^{10}$ and R$^{11}$ are identical or different and either represent straight-chain or branched alkyl having up to 8 carbon atoms, or together with the nitrogen atom represent a radical of the formula

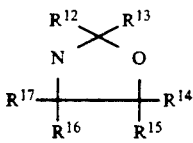

in which
R$^{12}$, R$^{13}$, R$^{14}$, R$^{15}$, R$^{16}$ and R$^{17}$ are identical or different and represent hydrogen, straight-chain or branched alkyl having up to 8 carbon atoms, aryl having 6 to 10 carbon atoms or cycloalkyl having 3 to 8 carbon atoms, or in each case one or more pairs of radicals selected from the group consisting of R$^{12}$ and R$^{13}$, R$^{14}$ and R$^{15}$, and R$^{16}$ and R$^{17}$ together form a 3- to 6-membered carbocycle, in an inert solvent with a selective base, in the presence of a chelate-forming diamine to give a compound of the formula

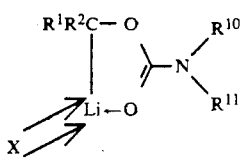
(III)

in which
X is a chiral or achiral diamine, then reacting this complex III with an electrophile of the formula

E—U in which
Y represents halogen,
E—Y together represent CO$_2$, an aliphatic or aromatic aldehyde or dialkylketone or an arylalkylketone, thereby to obtain a protected compound of the formula I'

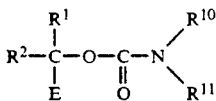
(I')

and in a last step, solvolytically removing the protecting group —CO—NR$^{10}$R$^{11}$,
wherein said deprotonation is carried out at a temperature range of from −100° C. to room temperature,
and at a pressure range of from 0.5 bar to 2 bar; the electrophilic substitution is carried out at a temperature range of from about −100° C.; to removal of the carbamate protecting group is carried out at normal pressure and a temperature range of from 0° C. to 130° C.; the base is used in the deprotonation step in a molar ration of from 0.5 to 5, based on the amount of the compound of Formula II, and the acids and bases used in removing the protecting groups are used in the molar ratio of from 0.01 to 10, based on the amount of the compound of Formula II.

2. A process according to claim 1,
in which
R$^1$ represents hydrogen or alkyl having 1–4 C atoms,
R$^2$ represents hydrogen,
E represents straight-chain or branched alkyl or alkenyl in each case having up to 4 carbon atoms which are optionally monosubstituted to trisubstituted by identical or different substituents from the group consisting of hydroxyl, phenyl, cyclobutyl, cyclohexyl and a group of the formula —NR$^3$R$^4$, —NH-CO—OR$^5$, —SiR$^6$R$^7$R$^8$ or —SnR$^{6'}$R$^{7'}$R$^{8'}$
in which
R$^3$ and R$^4$ are identical or different and denote hydrogen, straight-chain or branched alkyl having up to 4 carbon atoms or benzyl,
R$^5$ denotes methyl or ethyl which are optionally substituted by phenyl, and
R$^6$, R$^7$, R$^8$, R$^{6'}$, R$^{7'}$ and R$^{8'}$ represent methyl, or
E represents cyclobutyl or cyclohexyl which are optionally substituted by hydroxyl,
represents carboxyl, methoxycarbonyl or a group of the formula —SiR$^6$R$^7$R$^8$, —SnR$^{6'}$R$^{7'}$R$^{8'}$ or R$^9$—CO—,
and
R$^9$ denotes hydrogen or straight-chain or branched alkyl or alkenyl in each case having up to 4 carbon atoms which are optionally monosubstituted to trisubstituted by phenyl or by the group of the formula —NH—CO—OR$^5$.

3. A process according to claim 1, wherein the deprotonation is carried out at a temperature from −100° C. to room temperature.

4. A process according to claim 7, wherein the selective base is an alkyllithium compound.

5. A process according to claim 1, wherein the removal of the carbamate protecting groups is carried out at a temperature from about 0° C. to 130° C. in the presence of a strong acid or of an alkali metal or alkaline earth metal hydroxide.

* * * * *

UNITED STATES PATENT AND TRADEMARK OFFICE
CERTIFICATE OF CORRECTION

PATENT NO. : 5,223,633
DATED      : June 29, 1993
INVENTOR(S) : Hoppe, et al.

It is certified that error appears in the above-identified patent and that said Letters Patent is hereby corrected as shown below:

```
Col. 46, line 29    Delete " or " and substitute -- to --

Col. 47, line 34    Delete " E-U " and substitute -- E-Y --

Col. 48, line 3     After " 100° C " insert -- to + 40° C;--;
                    delete " to " and substitute -- the --

Col. 48, line 7     Delete " ration " and substitute -- ratio --

Col. 48, line 45    Delete " claim 7 " and substitute
                    -- claim 1 --
```

Signed and Sealed this

Eleventh Day of October, 1994

Attest:

BRUCE LEHMAN

*Attesting Officer*  *Commissioner of Patents and Trademarks*